United States Patent [19]

Palmaz

[11] Patent Number: 4,733,665
[45] Date of Patent: Mar. 29, 1988

[54] EXPANDABLE INTRALUMINAL GRAFT, AND METHOD AND APPARATUS FOR IMPLANTING AN EXPANDABLE INTRALUMINAL GRAFT

[75] Inventor: Julio C. Palmaz, San Antonio, Tex.

[73] Assignee: Expandable Grafts Partnership, San Antonio, Tex.

[21] Appl. No.: 796,009

[22] Filed: Nov. 7, 1985

[51] Int. Cl.$^4$ ............................................. A61M 29/00
[52] U.S. Cl. .................................... 128/343; 604/104; 604/96; 623/1
[58] Field of Search .............................. 128/343–344, 128/1 R; 623/1; 604/96, 104, 106–109

[56] References Cited

U.S. PATENT DOCUMENTS

| | | | |
|---|---|---|---|
| 2,701,559 | 2/1955 | Cooper | 128/344 |
| 3,774,596 | 11/1973 | Cook . | |
| 3,868,956 | 3/1975 | Alfidi et al. . | |
| 3,882,845 | 5/1975 | Bucalo | 128/1 R |
| 3,889,685 | 6/1975 | Miller et al. | 128/348 |
| 4,018,230 | 4/1977 | Ochiai et al. | 128/344 |
| 4,140,126 | 2/1979 | Choudhury . | |
| 4,141,364 | 2/1979 | Schultze . | |
| 4,183,102 | 1/1980 | Guiset | 3/1.4 |
| 4,299,226 | 11/1981 | Banka . | |
| 4,318,410 | 3/1982 | Chin . | |
| 4,416,028 | 11/1983 | Erikson et al. . | |
| 4,425,908 | 1/1984 | Simon . | |
| 4,483,339 | 11/1984 | Gillis . | |
| 4,483,340 | 11/1984 | Fogarty et al. | 128/344 |
| 4,503,569 | 3/1985 | Dotter | 3/1.4 |
| 4,512,338 | 4/1985 | Balko . | |
| 4,553,545 | 11/1985 | Maass . | |
| 4,560,374 | 12/1985 | Hammerslag . | |
| 4,562,596 | 1/1986 | Kornberg . | |
| 4,564,014 | 1/1986 | Fogarty et al. . | |
| 4,577,631 | 3/1986 | Kreamer . | |
| 4,580,568 | 4/1986 | Gianturco . | |
| 4,650,466 | 3/1987 | Luther | 604/266 |

FOREIGN PATENT DOCUMENTS 0183372  4/1986  European Pat. Off. .
2135585  9/1984  United Kingdom .

OTHER PUBLICATIONS

"Flexible Balloon-Expanded Stent for Small Vessels", Radiology, Jan. 1987, pp. 276–280, vol. 162, No. 1.
"Expandable Intraluminal Graft: A Preliminary Study"; Radiology Jul. 1985; paper presented at 70th Scientific Assembly and Annual Meeting of the Radiological Society of North America, Nov. 25, 1984, by Julio C. Palmaz et al.
"Percutaneous Endovascular Stents: An Experimental Evaluation"; Wright et al., Radiology 156; 1985.
"Transluminal Expandable Nitinol Coil Stent Grafting: Preliminary Report" Dotter et al.; Radiology 147; 1983.
"Non Surgical Placement of Arterial Endoprostheses: A New Technique Using Nitinol Wire"; Cragg et al.; Radiology 147, 1983.
"Transluminally-Placed Coilspring Endurtorial Tube Grafts"; Dotter Investigative Radiology; Sep.–Oct. 1969.
"Radio Logical Follow-Up of Transluminally Inserted Vascular Endoprostheses: An Experimental Study Using Expanding Spirals"; Radiology 152; 1984.

Primary Examiner—C. Fred Rosenbaum
Assistant Examiner—Gene B. Kartchner
Attorney, Agent, or Firm—Ben D. Tobor

[57] ABSTRACT

An expandable intraluminal vascular graft is expanded within a blood vessel by an angioplasty balloon associated with a catheter to dilate and expand the lumen of a blood vessel. The graft may be a wire mesh tube.

28 Claims, 6 Drawing Figures

EXPANDABLE INTRALUMINAL GRAFT, AND METHOD AND APPARATUS FOR IMPLANTING AN EXPANDABLE INTRALUMINAL GRAFT

Field of the Invention

The government of the United States of America retains a non-exclusive, irrevocable, royalty-free license in this invention for all governmental purposes, pursuant to 37 C.F.R. §100.6(b) (2).

The invention relates to an expandable intraluminal graft for use within a body passageway or duct and, more particularly, expandable intraluminal vascular grafts which are particularly useful for repairing blood vessels narrowed or occluded by disease; and a method and apparatus for implanting expandable intraluminal grafts.

Description of the Prior Art

Intraluminal endovascular grafting has been demonstrated by experimentation to present a possible alternative to conventional vascular surgery. Intraluminal endovascular grafting involves the percutaneous insertion into a blood vessel of a tubular prosthetic graft and its delivery via a catheter to the desired location within the vascular system. Advantages of this method over conventional vascular surgery include obviating the need for surgically exposing, incising, removing, replacing, or bypassing the defective blood vessel.

Structures which have previously been used as intraluminal vascular grafts have included coiled stainless steel springs; helically wound coil springs manufactured from an expandable heat-sensitive material; and expanding stainless steel stents formed of stainless steel wire in a zig-zag pattern. In general, the foregoing structures have one major disadvantage in common. Insofar as these structures must be delivered to the desired location within a given body passageway in a collapsed state, in order to pass through the body passageway, there is no effective control over the final, expanded configuration of each structure. For example, the expanison of a particular coiled spring-type graft is predetermined by the spring constant and modulus of elasticity of the particular material utilized to manufacture the coiled spring structure. These same factors predetermine the amount of expansion of collapsed stents formed of stainless steel wire in a zig-zag pattern. In the case of intraluminal grafts, or prostheses, formed of a heat sensitive material which expands upon heating, the amount of expansion is likewise predetermined by the heat expansion characteristics of the particular alloy utilized in the manufacture of the intraluminal graft.

Thus, once the foregoing types of intraluminal grafts are expanded at the desired location within a body passageway, such as within an artery or vein, the expanded size of the graft cannot be changed. If the diameter of the desired body passageway has been miscalculated, an undesized graft might not expand enough to contact the interior surface of the body passageway, so as to be secured thereto. It may then migrate away from the desired location within the body passageway. Likewise, an oversized graft might expand to such an extent that the spring force, or expansion force, exerted by the graft upon the body passageway could cause rupturing of the body passageway.

Another alternative to conventional vascular surgery has been percutaneous balloon dilation of elastic vascular stenoses, or blockages, through use of a catheter mounted angioplasty balloon. In this procedure, the angioplasty balloon is inflated within the stenosed vessel, or body passageway, in order to shear and disrupt the wall components of the vessel to obtain an enlarged lumen. With respect to arterial atheroscleerotic lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or block the lumen. Typically, the distending intraluminal pressure within the body passageway can hold the disrupted layer, or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct this problem.

Although the balloon dilation procedure is typically conducted in the catheterization lab of a hospital, because of the foregoing problem, it is always necessary to have a surgeon on call should the intimal flap block the blood vessel or body passageway. Further, because of the possibility of the intimal flap tearing away from the blood vessel and blocking the lumen, balloon dilations cannot be performed upon certain critical body passageways, such as the left main coronary artery, which leads into the heart. If an intimal flap formed by a balloon dilation procedure abruptly comes down and closes off a critical body passageway, such as the left main coronary artery, the patient could die before any surgical procedures could be performed.

Additional disadvantages associated with balloon dilation of elastic vascular stenoses is that many fail because of elastic recoil of the stenotic lesion. This usually occurs due to a high fibrocollagenous content in the lesion and is sometimes due to certain mechanical characteristics of the area to be dilated. Thus, although the body passageway may initially be successfully expanded by a balloon dilation procedure, subsequent, early restenosis can occur due to the recoil of the body passageway wall which decreases the size of the previously expanded lumen of the body passageway. For example, stenoses of the renal artery at the ostium are known to be refractory to balloon dilation because the dilating forces are applied to the aortic wall rather than to the renal artery itself. Vascular stenoses caused by neointimal fibrosis, such as those seen in dialysis-access fistulas, have proved to be difficult to dilate, requiring high dilating pressures and larger balloon diameters. Similar difficulties have been observed in angioplasties of graft-artery anastomotic strictures and postendarterectomy recurrent stenoses. Percutaneous angioplasty of Takayasu arteritis and neurofibromatosis arterial stenoses may show poor initial response and recurrence which is believed due to the fibrotic nature of these lesions.

Accordingly, prior to the development of the present invention, there has been no expandable intraluminal vascular graft, and method and apparatus for expanding the lumen of a body passageway, which: prevents recurrence of stenoses in the body passageway; can be utilized for critical body passageways, such as the left main coronary artery of a patient's heart; prevents recoil of the body passageway wall; and allows the intraluminal graft to be expanded to a variable size to prevent migration of the graft away from the desired location; and to prevent rupturing of the body passageway by the expanded graft. Therefore, the art has sought an expandable intraluminal vascular graft, and method and apparatus for expanding the lumen of a body passageway which: prevents recurrence of stenoses in the body passageway; is believed to be able to be utilized in critical body passageways, such as the left main coronary artery of the heart; prevents recoil of the body passageway; and can be expanded to a variable size within the body passageway to prevent migration of the graft away from the desired location; and to prevent rupturing of the body passageway by the expanded graft.

SUMMARY OF THE INVENTION

In accordance with the invention the foregoing advantages have been achieved through the present expandable intraluminal vascular graft. The present invention includes a tubular shaped member having first and second ends and a wall surface disposed between the first and second ends, the wall surface being formed by a plurality of intersecting elongate members, at least some of the elongate members intersecting with one another intermediate the first and second ends of the tubular shaped member; the tubular shaped member having a first diameter which permits intraluminal delivery of the tubular shaped member into a body passageway having a lumen; and the tubular shaped member having a second, expanded diameter, upon the application from the interior of the tubular shaped member of a radially, outwardly extending force, which second diameter is variable and dependent upon the amount of force applied to the tubular shaped member, whereby the tubular shaped member may be expanded to expand the lumen of the body passageway.

A further feature of the present invention is that the plurality of elongate members may be a plurality of wires, and the wires may be fixedly secured to one another where the wires intersect with one another. An additional feature of the present invention is that the plurality of elongate members may be a plurality of thin bars which are fixedly secured to one another where the bars intersect with one another. A further feature of the present invention is that the tubular shaped member may have a biologically inert coating on its wall surface, and the coating may include a means for anchoring the tubular shaped member to the body passageway.

In accordance with the invention, the foregoing advantages have also been achieved through the present method for expanding the lumen of a body passageway. The method of the present invention comprises the steps of: inserting an intraluminal graft, disposed upon a catheter, into the body passageway until it is disposed adjacent a desired location within the body passageway; and expanding a portion of the catheter to cause the intraluminal graft to radially expand outwardly into contact with the body passageway until the lumen of the body passageway at the desired location of the body passageway has been expanded, whereby the intraluminal graft prevents the body passageway from collapsing and decreasing the size of the expanded lumen.

A further feature of the present invention is that the portion of the catheter in contact with the intraluminal graft may be collapsed, and the catheter removed from the body passageway. A further feature of the present invention is that a catheter having an expandable, inflatable portion associated therewith may be utilized; and expansion of the intraluminal graft and the portion of the catheter is accomplished by inflating the expandable, inflatable portion of the catheter.

A further feature of the present invention is that a wire mesh tube may be utilized as the intraluminal graft, the wire mesh tube having a first predetermined, collapsed diameter which permits the tube to be inserted within the body passageway at and delivered to the desired location. Another feature of the present invention is that the wire mesh tube may be expanded to a second diameter within the body passageway; the second, expanded diameter being variable and determined by the desired expanded internal diameter of the body passageway, whereby the expanded wire mesh tube will not migrate from the desired location within the body passageway and the expansion of the intraluminal graft does not cause a rupture of the body passageway.

In accordance with the invention, the foregoing advantages have also been achieved through the present apparatus for intraluminally reinforcing a body passageway. The present invention includes: an expandable, tubular shaped prosthesis having first and second ends and a wall surface disposed between the first and second ends, the wall surface being formed by a plurality of intersecting elongate members; and a catheter, having an expandable, inflatable portion associated therewith and including means for mounting and retaining the expandable tubular shaped prosthesis on the expandable, inflatable portion, whereby upon inflation of the expandable, inflatable portion of the catheter, the prosthesis is forced radially into contact with the body passageway. A further feature of the present invention is that the mounting and retaining means may comprise a retainer ring member disposed on the catheter adjacent the expandable, inflatable portion and adjacent each end of the expandable, tubular shaped prosthesis.

The expandable intraluminal vascular graft, method for expanding the lumen of a body passageway, and apparatus for intraluminally reinforcing a body passageway of the present invention, when compared with previously proposed prior art intraluminal grafts, methods for implanting them, and balloon dilation techniques have the advantages of: preventing recurrence of stenoses; is believed to permit implantation of grafts in critical body passageways, such as in the left main coronary artery of the heart; prevents recoil of the body passageway; and permits expansion of the graft to a variable size dependent upon conditions within the body passageway.

When the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

Figure 1A:
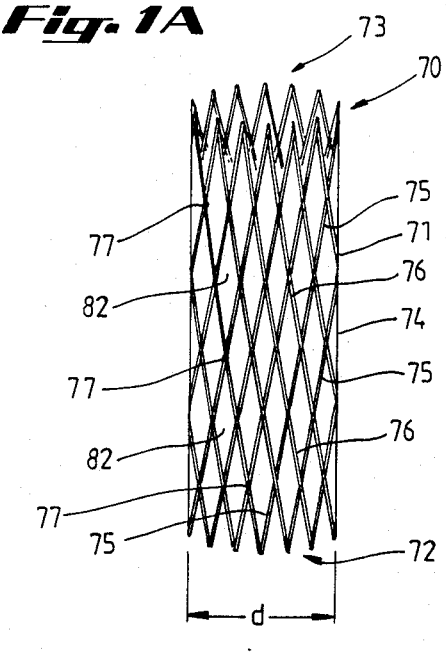
FIG. 1A is a perspective view of an expandable intraluminal vascular graft, or prosthesis for a body passageway, having a first diameter which permits delivery of the graft, or prosthesis, into a body passageway.
Figure 2A:
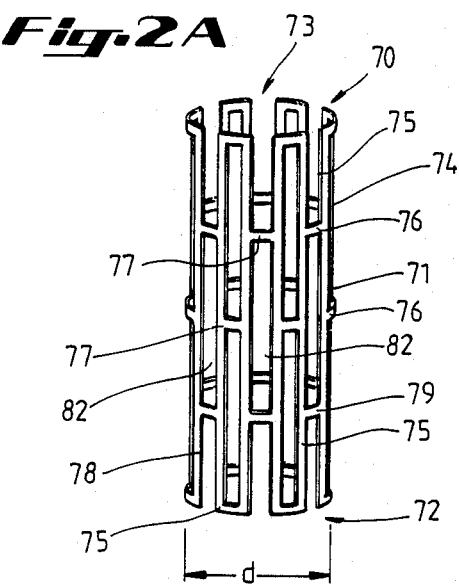
FIG. 2A is a perspective view of another embodiment of an expandable intraluminal vascular graft, or prosthesis for a body passageway, having a first diameter which permits intraluminal delivery of the graft, or prosthesis, into a body passageway.

In FIGS. 1A and 2A, an expandable intraluminal vascular graft, or expandable prosthesis for a body passageway, 70 is illustrated. It should be understood that the terms "expandable intraluminal vascular graft" and "expandable prosthesis" are interchangeably used to some extent in describing the present invention, insofar as the methods, apparatus, and structures of the present invention may be utilized not only in connection with an expandable intraluminal vascular graft for expanding partially occluded segments of a blood vessel, or body passageway, but may also be utilized for many other purposes as an expandable prosthesis for many other types of body passageways. For example, expandable prostheses 70 may also be used for such purposes as: (1) supportive graft placement within blocked arteries opened by transluminal recanalization, but which are likely to collapse in the absence of an internal support; (2) similar use following catheter passage through mediastinal and other veins occluded by inoperable cancers; (3) reinforcement of catheter created intrahepatic communications between portal and hepatic veins in patients suffering from portal hypertension; (4) supportive graft placement of narrowing of the esophagus, the intestine, the ureters, the urethra; and (5) supportive graft reinforcement of reopened and previously obstructed bile ducts. Accordingly, use of the term "prosthesis" encompasses the foregoing usages within various types of body passageways, and the use of the term "intraluminal vascular graft" encompasses use for expanding the lumen of a body passageway. Further, in this regard, the term "body passageway" encompasses any duct within the human body, such as those previously described, as well as any vein, artery, or blood vessel within the human vascular system.

Figure 1B:
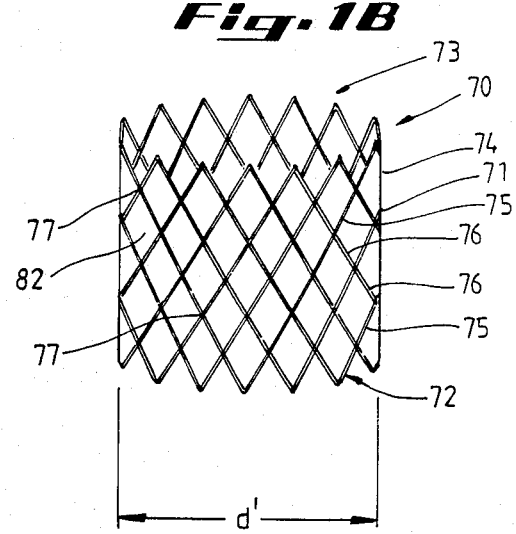
FIG. 1B is a perspective view of the graft, or prosthesis, of FIG. 1A, in its expanded configuration when disposed within a body passageway.
Figure 3:
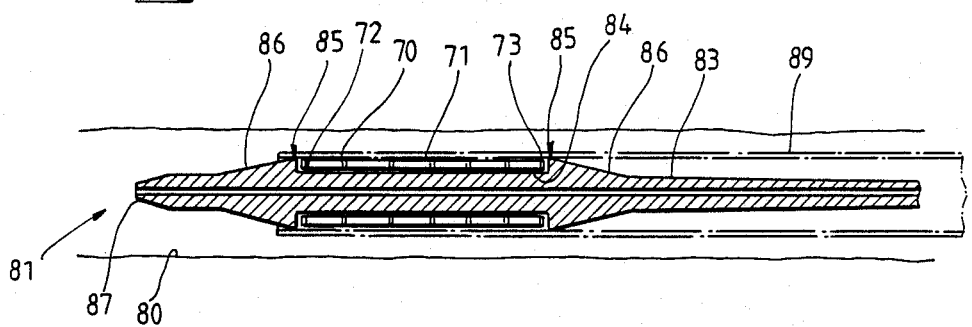
FIG. 3 is a cross-sectional view of an apparatus for intraluminally reinforcing a body passageway, or for expanding the lumen of a body passageway, illustrating a prosthesis, or intraluminal vascular graft, in the configurations shown in FIGS. 1A and 2A.

Still with reference to FIG. 1A, the expandable intraluminal vascular graft, or prosthesis, 70 is shown to generally comprise a tubular shaped member 71 having first and second ends 72, 73 and a wall surface 74 disposed between the first and second ends 72, 73. Preferably, the wall surface 74 is formed by a plurality of intersecting elongate members 75, 76 with at least some of the elongate members 75, 76 intersecting with one another intermediate the first and second ends 72, 73 of the tubular shaped member 71, such as shown at intersection points 77. Tubular shaped member 71 has a first diameter, d, which, to be hereinafter described in greater detail, permits intraluminal delivery of the tubular shaped member 71 into a body passageway 80 having a lumen (FIG. 3). With reference to FIG. 1B, upon the application from the interior of the tubular shaped member 71 of a radially, outwardly extending force, to be hereinafter described in greater detail, tubular shaped member 71 has a second, expanded diameter, d', which second diameter d' is variable in size and dependent upon the amount of force applied to the tubular shaped member 71.

With reference to FIGS. 1A and 1B, elongate members 75, 76, which form wall surface 74 of tubular shaped member 71, may be any suitable material which is compatible with the human body and the bodily fluids (not shown) with which the vascular graft, or prosthesis, 70 may come into contact. Elongate members 75, 76 must also be made of a material which has the requisite strength and elasticity characteristics to permit the tubular shaped member 71 to be expanded from the configuration shown in FIG. 1A to the configuration shown illustrated in FIG. 1B and further to permit the tubular shaped member 71 to retain its expanded configuration with the enlarged diameter d' shown in FIG. 1B. Suitable materials for the fabrication of tubular shaped member 71 would include silver, tantalum, stainless steel, gold, titanium or any suitable plastic material having the requisite characteristics previously described. Preferably, elongate members 75, 76 are fabricated from stainless steel. Preferably, the elongate members 75, 76 illustrated in FIGS. 1A and 1B are small diameter stainless steel wires having a cylindrical cross-section. It should of course be understood that each elongate member 75, 76, could have other cross-sectional configurations, such as triangular, square, rectangular, hexagonal, etc. Further, it is preferable that the plurality of elongate members 75, 76 are fixedly secured to one another where the elongate members 75, 76 intersect with one another, such as at the intersection points 77. Elongate members 75, 76 could be fixedly secured to one another in any conventional manner, such as by welding, soldering, or gluing, such as with a suitable epoxy glue; however, it is preferred that the intersection points 77 are soldered with silver. By fixedly securing the elongate members 75, 76, to one another, tubular member 71 is provided with a relatively high resistance to radial collapse, and the tubular shaped member 71 has the ability to retain its enlarged diameter, d', as shown in FIG. 1B. Preferably, tubular shaped member 71 is made of continuous, stainless steel wire woven in a criss-crossed tubular pattern to form what can be generally described as a wire mesh tube.

When fabricating tubular shaped member, or wire mesh tube, 71, it can be initially fabricated in the configuration shown in FIG. 1A with diameter, d. Alternatively, it can be fabricated with a diameter which is larger than initial diameter d and after fabrication, tubular shaped member 71 could be carefully collapsed to have diameter d shown in FIG. 1A. During the collapsing of tubular shaped member, or wire mesh tube, 71, care must be taken to insure that overlapping of adjacent elongate members 75, 76 is avoided. It should of course be understood that upon expansion of tubular shaped member, or wire mesh tube, 71 into the configuration shown in FIG. 1B, the distance between first and second ends 72 and 73 will of course decrease.

Figure 2B:
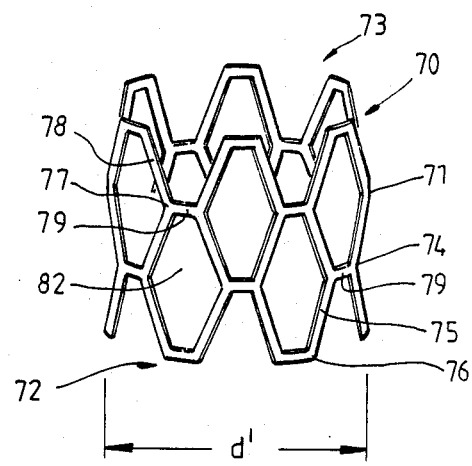
FIG. 2B is a perspective view of the graft, or prosthesis, of FIG. 2A, shown in its expanded configuration when disposed within a body passageway.

With reference now to FIGS. 2A and 2B, another embodiment of expandable intraluminal vascular graft, or prosthesis, 70, is illustrated. The same reference numerals are utilized and are applicable for elements previously described in FIGS. 1A and 1B. The intraluminal vascular graft, or prosthesis, 70 of FIGS. 2A and 2B differs from that previously described in connection with FIGS. 1A and 1B, in that the plurality of elongate members 75 and 76 are a plurality of thin bars 78, 79 which are preferably fixedly secured to one another where the bars 78, 79 intersect with one another. Bars 78, 79 preferably have a thin, rectangular cross-sectional configuration, and may be joined to one another in any conventional manner, such as by welding, brazing, soldering, or may be formed integral with one another. Preferably, tubular shaped member 71 is initially a thin-walled stainless steel tube, and the openings 82 between the intersecting bars 78 and 79 are formed by a conventional etching process, such as electromechanical or laser etching, whereby the resultant structure is a tubular shaped member 71 having a plurality of intersecting elongate members 78, 79. The embodiment of graft, or prosthesis, 70 of FIG. 2A, likewise can assume an expanded configuration as shown in FIG. 2B and as previously described in connection with FIG. 1B, upon the application from the interior of the tubular shaped member 71 of a radially, outwardly extending force. It should be further understood that the embodiment of vascular graft, or prosthesis, 70 of FIGS. 2A and 2B, could also be generally described as a wire mesh tube.

Figure 4:
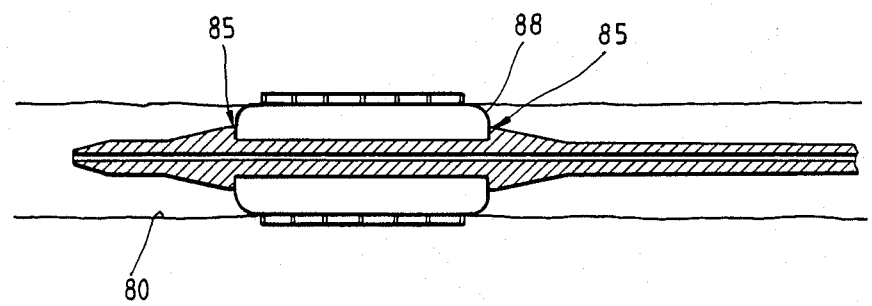
FIG. 4 is a cross-sectional view of the apparatus for intraluminally reinforcing a body passageway, or for expanding the lumen of a body passageway, with a graft, or prosthesis, in the configurations shown in FIGS. 1B and 2B.

With reference now to FIGS. 3 and 4, the methods and apparatus of the present invention will be described in greater detail. Once again, it should be understood that the methods and apparatus of the present invention are useful not only for expanding the lumen of a body passageway, such as an artery, vein, or blood vessel of the human vascular system, but are also useful to perform the previously described procedures to intraluminally reinforce other body passageways or ducts, as previously described. Still with reference to FIGS. 3 and 4, an expandable intraluminal vascular graft, or prosthesis, 70, which may be of the type previously described in connection with FIGS. 1A or 2A, is disposed or mounted upon a catheter 83. Catheter 83 has an expandable, inflatable portion 84 associated therewith. Catheter 83 includes means for mounting and retaining 85 the expandable intraluminal vascular graft, or prosthesis, 70 on the expandable, inflatable portion 84 of catheter 83. Preferably, the mounting and retaining means 85 comprises retainer ring members 86 disposed on the catheter 83 adjacent the expandable inflatable portion 84 of catheter 83; and a retainer ring member 86 is disposed adjacent each end 72, 73 of the expandable intraluminal vascular graft, or prosthesis, 70. Preferably, as seen in FIG. 3, while retainer ring members are formed integral with catheter 83, and the retainer ring member 86 adjacent the leading tip 87 of catheter 83 slopes upwardly and away from catheter tip 87 in order to protect and retain graft or prosthesis, 70 as it is inserted into the lumen 81 of body passageway 80, as to be hereinafter described in greater detail. The remaining retainer ring member 86 as shown in FIG. 3, slopes downwardly away from tip 87 of catheter 83, to insure easy removal of catheter 83 from body passageway 80. After expandable intraluminal graft, or prosthesis, 70 has been disposed upon catheter 83, in the manner previously described, the graft, or prosthesis, 70 and catheter 83 are inserted within a body passageway 80 by catheterization of the body passageway 80 in a conventional manner.

In a conventional manner, the catheter 83 and graft, or prosthesis, 70 are delivered to the desired location within the body passageway 80, whereat it is desired to expand the lumen 81 of body passageway 80 via intraluminal graft 70, or where it is desired to implant prosthesis 70. Fluoroscopy, and/or other conventional techniques may be utilized to insure that the catheter 83 and graft, or prosthesis, 70 are delivered to the desired location within the body passageway. Prosthesis, or graft, 70 are then expanded by expanding the expandable, inflatable portion 84 of catheter 83, whereby the prosthesis, or graft, 70 is forced radially, outwardly into contact with the body passageway 80 as shown, in FIG. 4. In this regard, the expandable, inflatable portion of catheter 83 may be a conventional angioplasty balloon 88. After the desired expansion of prosthesis, or graft, 70 has been accomplished, angioplasty balloon 88 may be collapsed, or deflated, and the catheter 83 may be removed in a conventional manner from body passageway 80. If desired, as seen in FIG. 3, catheter 83, having graft or prosthesis, 70 disposed thereon, may be initially encased in a conventional Teflon TM sheath 89, which is pulled away from prosthesis, or graft, 70, prior to expansion of the prosthesis, or graft, 70.

Still with reference to FIGS. 3 and 4, it should be noted that the tubular shaped member 71 of prosthesis, or graft, 70 initially has the first predetermined, collapsed diameter d as described in connection with FIGS. 1A and 2A, in order to permit the insertion of the wire mesh tube, or tubular shaped member, 71 into the body passageway 80 as previously described. When it is desired to implant prosthesis 70 within a body passageway 80 for the purposes previously described, the wire mesh tube, or prosthesis 70, is expanded to the second diameter d' and the second, expanded diameter d' is variable and determined by the internal diameter of the body passageway 80, as shown in FIG. 4. Accordingly, the expanded prosthesis 70, upon deflation of angioplasty balloon 88 will not be able to migrate from the desired location within the body passageway 80, nor will the expansion of the prosthesis 70 be likely to cause a rupture of the body passageway 80.

When it is desired to use expandable intraluminal graft 70 to expand the lumen 81 of a body passageway 80 having an area of stenosis, the expansion of intraluminal vascular graft 70 by angioplasty balloon 88, allows controlled dilation of the stenotic area and, at the same time controlled expansion of the vascular graft 70, whereby vascular graft 70 prevents the body passageway 80 from collapsing and decreasing the size of the previously expanded lumen 81. Once again, the second, expanded diameter d' of intraluminal vascular graft 70, as shown in FIG. 4 is variable and determined by the desired expanded internal diameter of body passageway 80. Thus, the expandable intraluminal graft 70 will not migrate away from the desired location within the body passageway 80 upon deflation of angioplasty balloon 88, nor will the expansion of intraluminal graft 70 likely cause a rupture of body passageway 80. Further, should an intimal flap, or fissure, be formed in body passageway 80 at the location of graft 70, graft 70 will insure that such an intimal flap will not be able to fold inwardly into body passageway 80, nor tear loose and flow through body passageway 80. In the situation of utilizing graft 70 in the manner previously described to expand the lumen of a portion of the left main artery, it is believed that the intimal flap will be unable to enter the heart and cause the death of the patient.

Because it is only necessary to inflate angioplasty balloon 88 one time in order to expand graft 70, it is believed that a greater amount of endothelium, or inner layer of the intima, or inner surface of the body passageway, will be preserved, insofar as the extent of endothelial denudation during transluminal angioplasty is proportional to the balloon inflation time. Further, in theory, the amount of preserved endothelium should be large because in the expanded configuration of graft 70, potentially 80% of the endothelium is exposed through openings 82 of graft 70. It is further believed that intact patches of endothelium between the elongate members 75, 76, 78, 79 of graft 70 may result in a rapid, multicentric endothelialization pattern as shown by experimental studies.

It is to be understood that the invention is not limited to the exact details of construction, operation, exact materials or embodiment shown and described, as obvious modifications and equivalents will be apparent to one skilled in the art. For example, the means for expanding the prosthesis or graft could be a plurality of hydraulically actuated rigid members disposed on a catheter, or a plurality of angioplasty balloons could be utilized to expand the prosthesis or graft. Accordingly, the invention is therefore to be limited only by the scope of the appended claims.

What is claimed is:

1. A method for implanting a prosthesis within a body passageway comprising the steps of:
   disposing the prosthesis upon a catheter;
   inserting the prosthesis and catheter within the body passageway by catheterization of said body passageway; and
   providing controllable expansion of the prosthesis at a desired location within the body passageway by expanding a portion of the catheter associated with the prosthesis to force the prosthesis radially outwardly into contact with the body passageway, by deforming a portion of the prosthesis with a force in excess of the elastic limit of the portion of the prosthesis, to implant the prosthesis within the body passageway.

2. The method of claim 1, further including the steps of: collapsing the portion of the catheter associated with the prosthesis, and removing the catheter from the body passageway.

3. The method of claim 1, including the steps of: utilizing a catheter having an expandable, inflatable portion associated therewith; and the controllable expansion of the prosthesis and the portion of the catheter is accomplished by inflating the expandable, inflatable portion of the catheter.

4. The method of claim 1, including the step of: utilizing a wire mesh tube as the prosthesis, the wire mesh tube having a first predetermined collapsed diameter which permits the tube to be disposed upon the catheter and inserted into the body passageway.

5. The method of claim 4, wherein tantalum is utilized for the wire mesh tube.

6. The method of claim 4, wherein the wire mesh tube is expanded to a second diameter within the body passageway; the second, expanded diameter being variable and determined by the internal diameter of the body passageway, whereby the expanded wire mesh tube will not migrate from the desired location within the body passageway and the expansion of the prosthesis does not cause a rupture of the body passageway.

7. A method for expanding the lumen of a body passageway comprising the steps of:
   inserting an intraluminal graft, disposed upon a catheter, into the body passageway until it is disposed adjacent a desired location within the body passageway; and
   expanding a portion of the catheter to provide controllable expansion of the intraluminal graft radially, outwardly into contact with the body passageway, by deforming a portion of the intraluminal graft with a force in excess of the elastic limit of the portion of the prosthesis, until the lumen of the body passageway at the desired location in the body passageway has been expanded, whereby the intraluminal graft prevents the body passageway from collapsing and decreasing the size of the expanded lumen, and the intraluminal graft remains in the passageway.

8. The method of claim 7, further including the steps of: collapsing the portion of the catheter in contact with the intraluminal graft and removing the catheter from the body passageway.

9. The method of claim 7, including the steps of: utilizing a catheter having an expandable, inflatable portion associated therewith; and the controllable expansion of the intraluminal graft and the portion of the catheter is accomplished by inflating the expandable, inflatable portion of the catheter.

10. The method of claim 7, including the step of: utilizing a wire mesh tube as the intraluminal graft, the wire mesh tube having a first predetermined, collapsed diameter which permits the tube to be inserted within the body passageway at the desired location.

11. The method of claim 10, wherein tantalum is utilized for the wire mesh tube.

12. The method of claim 10, wherein the wire mesh tube is expanded to a second diameter within the body passageway; the second, expanded diameter being variable and determined by the desired expanded internal diameter of the body passageway, whereby the expanded wire mesh tube will not migrate from the desired location within the body passageway and the expansion of the intraluminal graft does not cause a rupture of the body passageway.

13. An expandable intraluminal vascular graft, comprising:
   a tubular shaped member having first and second ends and a wall surface disposed between the first and second ends, the wall surface being formed by a plurality of intersecting elongate members, at least some of the elongate members intersecting with one another intermediate the first and second ends of the tubular shaped member;
   the tubular shaped member having a first diameter which permits intraluminal delivery of the tubular shaped member into a body passageway having a lumen; and
   the tubular shaped member having a second, expanded diameter, upon the application from the interior of the tubular shaped member of a radially, outwardly extending force, which second diameter is variable and controlled by the amount of force applied to the tubular shaped member, at least some of the elongate members being deformed by the radially, outwardly extending force, to retain the tubular shaped member with the second, expanded diameter, whereby the tubular shaped member may be expanded to expand the lumen of the body passageway and remain therein.

14. The expandable intraluminal vascular graft of claim 13, wherein the plurality of elongate members are a plurality of wires, and the wires are fixedly secured to one another where the wires intersect with one another.

15. The expandable intraluminal vascular graft of claim 14, wherein the plurality of elongate members are a plurality of tantalum wires.

16. The expandable intraluminal vascular graft of claim 13 wherein the plurality of elongate members are a plurality of thin bars which are fixedly secured to one another where the bars intersect with one another.

17. The expandable intraluminal vascular graft of claim 16, wherein the plurality of elongate members are a plurality of thin tantalum bars.

18. An expandable prosthesis for a body passageway, comprising:
a tubular shaped member having first and second ends and a wall surface disposed between the first and second ends, the wall surface being formed by a plurality of intersecting elongate members, at least some of the elongate members intersecting with one another intermediate the first and second ends of the tubular shaped member;
the tubular shaped member having a first diameter which permits intraluminal delivery of the tubular shaped member into a body passageway having a lumen; and
the tubular shaped member having a second, expanded diameter, upon the application from the interior of the tubular shaped member of a radially, outwardly extending force, which second diameter is variable and controlled by the amount of force applied to the tubular shaped member, at least some of the elongate members being deformed by the radially, outwardly extending force, to retain the tubular shaped member with the second, expanded diameter, whereby the tubular shaped member may be expanded to expand the lumen of the body passageway and remain therein.

19. The expandable prosthesis for a body passageway of claim 18, wherein the plurality of elongate members are a plurality of wires and the wires are fixedly secured to one another where the wires intersect with one another.

20. The expandable prosthesis of claim 19, wherein the plurality of elongate members are a plurality of tantalum wires.

21. The expandable prosthesis for a body passageway of claim 18, wherein the plurality of elongate members are a plurality of thin bars which are fixedly secured to one another where the bars intersect with one another.

22. The expandable prosthesis of claim 21, wherein the plurality of elongate members are a plurality of thin tantalum bars.

23. An apparatus for intraluminally reinforcing a body passageway, comprising:
an expandable, tubular shaped prosthesis having first and second ends, and a wall surface disposed between the first and second ends, the wall surface being formed by a plurality of intersecting elongate members, the expansion of the prosthesis being controllable; and
a catheter, having an expandable, inflatable portion associated therewith and including means for mounting and retaining the expandable, tubular shaped prosthesis on the expandable, inflatable portion,
whereby upon inflation of the expandable, inflatable portion of the catheter, the prosthesis is forced radially outwardly into contact with the body passageway to remain therein, and the expansion of the prosthesis is controlled by the expansion of the inflatable portion of the catheter.

24. The apparatus of claim 23, wherein the plurality of intersecting elongate members are a plurality of intersecting elongate, tantalum members.

25. The apparatus of claim 23, wherein the mounting and retaining means comprises retainer ring members disposed on the catheter adjacent the expandable, inflatable portion and adjacent each end of the expandable, tubular shaped prosthesis.

26. An apparatus for expanding the lumen of a body passageway comprising:
an expandable intraluminal vascular graft having first and second ends, and a wall surface disposed between the first and second ends, the wall surface being formed by a plurality of intersecting elongate members, the expansion of the vascular graft being controllable; and
a catheter, having an expandable, inflatable portion associated therewith and including means for mounting and retaining the expandable intraluminal vascular graft on the expandable, inflatable portion
whereby upon inflation of the expandable, inflatable portion of the catheter, the intraluminal vascular graft is forced radially outwardly into contact with the body passageway to remain therein, and the expansion of the vascular graft is controlled by the expansion of the inflatable portion of the catheter.

27. The apparatus of claim 26, wherein the plurality of intersecting elongate members are a plurality of intersecting elongate, tantalum members.

28. The apparatus of claim 26, wherein the mounting and retaining means comprises retainer ring members disposed on the catheter adjacent the expandable, inflatable portion and adjacent each end of the expandable intraluminal vascular graft.

* * * * *

UNITED STATES PATENT AND TRADEMARK OFFICE

CERTIFICATE EXTENDING PATENT TERM
UNDER 35 U.S.C. § 156

PATENT NO.:     4,733,665

DATED:          March 29, 1988

INVENTOR:       Julio C. Palmaz

PATENT OWNER:   Expandable Grafts Partnership

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

182 DAYS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks

UNITED STATES PATENT AND TRADEMARK OFFICE
CERTIFICATE OF CORRECTION

PATENT NO. : B1-4,733,665
DATED : January 11, 1994
INVENTOR(S) : Julio C. Palmaz It is certified that error appears in the above-indentified patent and that said Letters Patent is hereby corrected as shown below:

Column 2

In Claim 29, Line 2, delete "cather", and insert --catheter--

In Claim 29, Line 2, delete "catheri-", and insert --catheteri---.

In Claim 30, Line 3, delete "catherization", and insert --catheterization--.

Signed and Sealed this

Sixth Day of December, 1994

Attest:

BRUCE LEHMAN

Attesting Officer

Commissioner of Patents and Trademarks

… … … US004733665B1

REEXAMINATION CERTIFICATE (2182nd)
United States Patent [19]
Palmaz

[11] B1 4,733,665
[45] Certificate Issued    Jan. 11, 1994

[54] EXPANDABLE INTRALUMINAL GRAFT, AND METHOD AND APPARATUS FOR IMPLANTING AN EXPANDABLE INTRALUMINAL GRAFT

[75] Inventor: Julio C. Palmaz, San Antonio, Tex.

[73] Assignee: Expandable Grafts Partnership, Antonio, Tex.

Reexamination Requests:
No. 90/002,493, Oct. 23, 1991
No. 90/002,638, Feb. 12, 1992

Reexamination Certificate for:
Patent No.: 4,733,665
Issued: Mar. 29, 1988
Appl. No.: 796,009
Filed: Nov. 7, 1985

[51] Int. Cl.$^5$ ............................................. A61M 29/00
[52] U.S. Cl. ................................... 606/108; 606/191; 604/96; 604/104; 623/1
[58] Field of Search ......................... 606/108, 191, 198

[56] References Cited

U.S. PATENT DOCUMENTS

| | | |
|---|---|---|
| 3,657,744 | 4/1972 | Ersek . |
| 4,140,126 | 2/1979 | Choudhury . |
| 4,299,226 | 11/1981 | Banka . |
| 4,328,811 | 5/1982 | Fogarty . |
| 4,338,942 | 7/1982 | Fogarty . |
| 4,403,612 | 9/1983 | Fogarty . |
| 4,503,569 | 3/1985 | Dotter . |
| 4,560,374 | 12/1985 | Hammerslag . |

FOREIGN PATENT DOCUMENTS

WO83/03752 11/1983 PCT Int'l Appl. .

OTHER PUBLICATIONS

Program Abstract for the 1984 Annual Meeting of the Radiological Society of North America: Palmaz et al., "Expandable Intraluminal Graft: A Preliminary Study:"—distributed to the public Oct. 1984.
Palmaz et al., "Expandable Intraluminal Graft: A Preliminary Study", Radiology, 1985: 156: 73-77.
Palmaz et al., "Atherosclerotic Rabbit Aortas: Expandable Intraluminal Grafting", Radiology 1986: 160:723.
Abstract of Journal of Biomedical Materials Research, Jul. 1979, 13(4) pp. 631-643.
Abstract of Journal of Orthodontistry, May 1983, 83(5), pp. 391-407.
Dotter, "Transluminally-placed Coilspring Endarterial Tube Grafts", Investigative radiology, Sep.-Oct. 1969, vol. 4, pp. 329-332.
Maass et al., "Radiological Follow-up of Transluminally Inserted Vascular Endoprostheses: An Experimental Study Using Expanding Spirals", Radiology 1984: 152: 659-663.
Dorland's Illustrated Medical Dictionary, 26th Ed., 1981, pp. 675 and 759.
"The Experimental Use of Steel Mesh Tubes For The Replacement of Arterial Segments" AMA Archives of Surgery, Jan. 1956, vol. 72, pp. 69-75, B. G. Lary et al.
Radiology, vol. 153P (Special Issue—Scientific Program For Nov. RSNA Meeting) p. 329, (Mailed to Public in Oct. of 1984).

*Primary Examiner*—Michael H. Thaler

[57] ABSTRACT

An expandable intraluminal vascular graft is expanded within a blood vessel by an angioplasty balloon associated with a catheter to dilate and expand the lumen of a blood vessel. The graft may be a wire mesh tube.

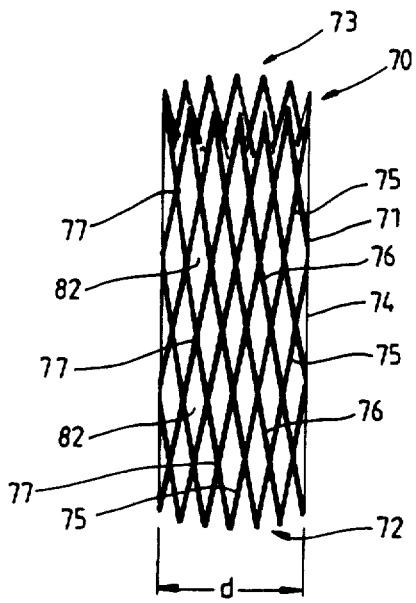

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 23-28 is confirmed.

Claims 1, 7, 13 and 18 are determined to be patentable as amended.

Claims 2-6, 8-12, 14-17 and 19-22, dependent on an amended claim, are determined to be patentable.

New claims 29-32 are added and determined to be patentable.

1. A method for implanting a prosthesis *at a desired location* within a body passageway comprising the steps of:
   disposing the prosthesis upon a catheter;
   inserting the prosthesis and catheter within the body passageway by catheterization of said body passageway; [and]
   *delivering the catheter and prosthesis through the body passageway to the desired location in the body passageway without surgically exposing the desired location of the body passageway; and*
   providing controllable expansion of the prosthesis at [a] *the* desired location within the body passageway by expanding a portion of the catheter associated with the prosthesis to force the prosthesis radially outwardly into contact with the body passageway, by deforming a portion of the prosthesis with a force in excess of the elastic limit of the portion of the prosthesis, to implant the prosthesis within the body passageway.

7. A method for expanding the lumen of a body passageway comprising the steps of:
   [inserting an intraluminal graft, disposed upon a catheter, into the body passageway until it is disposed adjacent a desired location within the body passageway; and]
   *disposing an intraluminal graft upon a catheter;*
   *inserting the intraluminal graft and catheter within the body passageway by catheterization of the body passageway;*
   *delivering the intraluminal graft and catheter through the body passageway to a desired location within the body passageway without surgically exposing the desired location of the body passageway; and*
   expanding a portion of the catheter to provide controllable expansion of the intraluminal graft radially, outwardly into contact with the body passageway, by deforming a portion of the intraluminal graft with a force in excess of the elastic limit of the portion of the [prosthesis] *intraluminal graft*, until the lumen of the body passageway at the desired location in the body passageway has been expanded, whereby the intraluminal graft prevents the body passageway from collapsing and decreasing the size of the expanded lumen, and the intraluminal graft remains in the *body* passageway.

13. An expandable intraluminal vascular graft, comprising:
   a tubular shaped member having first and second ends and a *smooth outer* wall surface, *without any narrow, outwardly projecting edges,* disposed between the first and second ends, the wall surface being formed by a plurality of intersecting elongate members, at least some of the elongate members intersecting with one another intermediate the first and second ends of the tubular shaped member;
   the tubular shaped member having a first diameter which permits intraluminal delivery of the tubular shaped member into a body passageway having a lumen; and
   the tubular shaped member having a second, expanded diameter *and a substantially smooth outer wall surface, without any narrow, outwardly projecting edges,* upon the application from the interior of the tubular shaped member of a radially, outwardly extending force, which second diameter is variable and controlled by the amount of force applied to the tubular shaped member, at least some of the elongate members being deformed by the radially, outwardly extending force to retain the tubular shaped member with the second, expanded diameter, whereby the tubular shaped member may be expanded to expand the lumen of the body passageway and remain therein.

18. An expandable prosthesis for a body passageway, comprising:
   a tubular shaped member having first and second ends and a *smooth outer* wall surface, *without any narrow, outwardly projecting edges,* disposed between the first and second ends, the wall surface being formed by a plurality of intersecting elongate members, at least some of the elongate members intersecting with one another intermediate the first and second ends of the tubular shaped member;
   the tubular shaped member having a first diameter which permits intraluminal delivery of the tubular shaped member into a body passageway having a lumen; and
   the tubular shaped member having a second, expanded diameter *and a substantially smooth outer wall surface, without any narrow outwardly projecting edges,* upon the application from the interior of the tubular shaped member of a radially, outwardly extending force, which second diameter is variable and controlled by the amount of force applied to the tubular shaped member, at least some of the elongate members being deformed by the radially, outwardly extending force, to retain the tubular shaped member with the second, expanded diameter, whereby the tubular shaped member may be expanded to expand the lumen of the body passageway and remain therein.

*29. The method of claim 1, wherein the prosthesis and cather are inserted within the body passageway by catherization through a body orifice.*

*30. The method of claim 1, wherein the prosthesis and catheter are inserted within the body passageway by percutaneous catherization of the body passageway.*

*31. The method of claim 7, wherein the intraluminal graft and catheter are inserted within the body passageway by catheterization through a body orifice.*

*32. The method of claim 7, wherein the intraluminal graft and catheter are inserted within the body passageway by percutaneous catheterization of the body passageway.*

* * * * *

(12) REEXAMINATION CERTIFICATE (4528th)
United States Patent
Palmaz

(10) Number: US 4,733,665 C2
(45) Certificate Issued: Jan. 29, 2002

(54) EXPANDABLE INTRALUMINAL GRAFT, AND METHOD AND APPARATUS FOR IMPLANTING AN EXPANDABLE INTRALUMINAL GRAFT

(75) Inventor: Julio C. Palmaz, San Antonio, TX (US)

(73) Assignee: Expandable Grafts Partnership, San Antonio, TX (US)

Reexamination Request:
No. 90/004,786, Oct. 6, 1997
No. 90/004,916, Feb. 15, 1998
No. 90/005,677, Mar. 15, 2000

Reexamination Certificate for:
Patent No.: 4,733,665
Issued: Mar. 29, 1988
Appl. No.: 06/796,009
Filed: Nov. 7, 1985

Certificate of Correction issued Dec. 6, 1994.

(51) Int. Cl.$^7$ ............................................. A61M 29/00
(52) U.S. Cl. ................... 606/108; 604/104; 604/96.01; 623/1.11; 623/1.15
(58) Field of Search ............................. 623/1.11, 1.15

(56) References Cited

U.S. PATENT DOCUMENTS

| | | | |
|---|---|---|---|
| 2,070,073 A | 2/1937 | Walton | 210/499 |
| 2,701,559 A | 2/1955 | Cooper | 128/2 |
| 2,854,982 A | 10/1958 | Pagano | 128/348 |
| 2,854,983 A | 10/1958 | Baskin | 604/96 |
| 3,334,629 A | 8/1967 | Cohn | 128/325 |
| 3,401,689 A | 9/1968 | Greenwood | |
| 3,526,005 A | * 9/1970 | Bokros et al. | 623/1 |
| 3,540,431 A | 11/1970 | Mobin-Udin | 128/1 R |
| 3,562,820 A | 2/1971 | Braun | 3/1 |
| 3,599,641 A | 8/1971 | Sheridan | 604/283 |
| 3,657,744 A | 4/1972 | Ersek | 128/334 |
| 3,774,596 A | 11/1973 | Cook | |
| 3,834,394 A | 9/1974 | Hunter et al. | 128/325 |
| 3,842,441 A | 10/1974 | Kaiser | |

(List continued on next page.)

FOREIGN PATENT DOCUMENTS

| | | |
|---|---|---|
| DE | 2 410 933 | 3/1974 |
| DE | 3205942 A1 | 9/1983 |
| EP | 183 372 | 10/1985 |
| EP | 0 177 330 A2 | 10/1986 |

(List continued on next page.)

OTHER PUBLICATIONS

Petition To Revoke European Patent No. 0 221 570 (UK) (Mar. 13, 1997).
Amended Particulars Of Objections (European Parent No. 0 221 570) (UK) (Oct. 27, 1997).
Plea Of Invalidity Of EP Patent 0 221 570 B1 (Italy) (Mar. 21, 1997).
Writ Of Summons In Nullity By Boston Scientific Of European patent Nos. 0 221 570 And 0 335 341 (France) (Mar. 17, 1997).
Writ Of Summons On Nullity By Saint–Come Of Eurpean Patent 0 221 570 B1 (France) (Mar. 12, 1997).
Brief Of Response Submitted By Dr. Palmaz (France) (Oct. 23, 1997).

(List continued on next page.)

*Primary Examiner*—Michael H. Thaler

(57) ABSTRACT

An expandable intraluminal vascular graft is expanded within a blood vessel by an angioplasty balloon associated with a catheter to dilate and expand the lumen of a blood vessel. The graft may be a wire mesh tube.

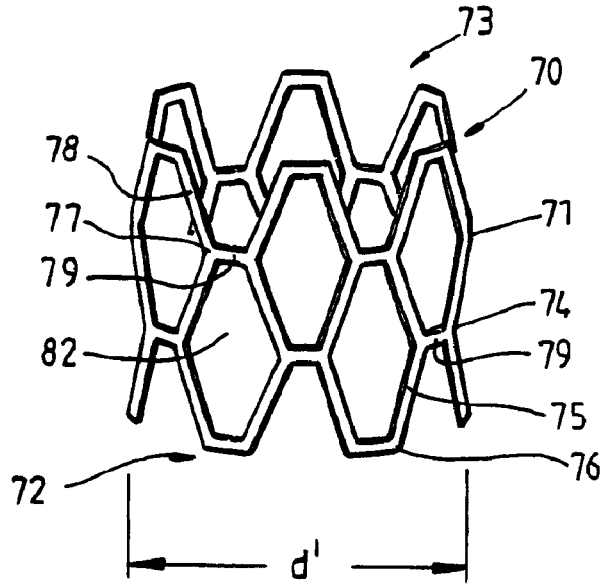

U.S. PATENT DOCUMENTS

| | | | |
|---|---|---|---|
| 3,858,441 A | 1/1975 | Comeau | 138/93 |
| 3,868,956 A | 3/1975 | Alfidi et al. | |
| 3,874,388 A | 4/1975 | King et al. | 128/334 |
| 3,882,845 A | 5/1975 | Bucalo | |
| 3,889,685 A | 6/1975 | Miller, Jr. et al. | |
| 3,952,747 A | 4/1976 | Kimmell, Jr. | 128/1 R |
| 3,968,800 A | 7/1976 | Vilasi | 128/343 |
| 4,018,230 A | 4/1977 | Ochiai et al. | 128/344 |
| 4,047,252 A | 9/1977 | Liebig et al. | 3/1.4 |
| 4,056,854 A | 11/1977 | Boretos et al. | 3/1.5 |
| 4,061,134 A | 12/1977 | Samuels et al. | 128/1 |
| 4,076,285 A | 2/1978 | Martinez | 285/332 |
| 4,105,022 A | 8/1978 | Anthoshkiw et al. | 128/2.05 F |
| 4,106,129 A | 8/1978 | Carpenter et al. | |
| 4,140,126 A | 2/1979 | Choudhury | 128/325 |
| 4,141,364 A | 2/1979 | Schultze | |
| 4,183,102 A | 1/1980 | Guiset | |
| 4,190,909 A | 3/1980 | Ablaza | 3/1.4 |
| 4,195,637 A | 4/1980 | Gruntzig et al. | 128/348 |
| 4,198,982 A | 4/1980 | Fortner et al. | 128/334 |
| 4,214,587 A | 7/1980 | Sakura, Jr. | 128/334 |
| 4,295,464 A | 10/1981 | Shihata | 128/1 |
| 4,299,226 A | 11/1981 | Banka | 128/344 |
| 4,300,244 A | 11/1981 | Bokros | 3/1.4 |
| 4,313,231 A | 2/1982 | Koyamada | 3/1.4 |
| 4,318,410 A | 3/1982 | Chin | |
| 4,319,363 A | 3/1982 | Ketharanathan | 3/1.4 |
| 4,328,811 A | 5/1982 | Fogarty | |
| 4,338,942 A | 7/1982 | Fogarty | |
| 4,340,046 A | 7/1982 | Cox | 128/207.17 |
| 4,390,599 A | 6/1983 | Broyles | 428/597 |
| 4,403,612 A | 9/1983 | Fogarty | |
| 4,416,028 A | 11/1983 | Eriksson et al. | |
| 4,425,908 A | 1/1984 | Simon | |
| 4,448,195 A | 5/1984 | LeVeen et al. | 128/344 |
| 4,479,497 A | 10/1984 | Fogarty | 128/344 |
| 4,483,339 A | 11/1984 | Gillis | |
| 4,483,340 A | 11/1984 | Fogarty et al. | |
| 4,493,711 A | 1/1985 | Chin et al. | 604/271 |
| 4,494,531 A | 1/1985 | Gianturco | 128/1 R |
| 4,503,569 A | 3/1985 | Dotter | 128/1 |
| 4,512,338 A | 4/1985 | Balko et al. | 128/1 |
| 4,531,933 A | 7/1985 | Norton et al. | 604/8 |
| 4,550,447 A | 11/1985 | Seiler, Jr. et al. | 623/1 |
| 4,553,545 A | 11/1985 | Maass et al. | |
| 4,560,374 A | 12/1985 | Hammerslag | 604/49 |
| 4,562,596 A | 1/1986 | Kornberg | |
| 4,564,014 A | 1/1986 | Fogarty et al. | |
| 4,572,186 A | 2/1986 | Gould et al. | 128/341 |
| 4,577,631 A * | 3/1986 | Kreamer | 623/12 |
| 4,580,568 A | 4/1986 | Gianturco | |
| 4,586,505 A | 5/1986 | Sisson et al. | 128/344 |
| 4,604,762 A | 8/1986 | Robinson | 623/1 |
| 4,617,932 A | 10/1986 | Kornberg | 128/334 |
| 4,619,261 A | 10/1986 | Guerriero | 128/325 |
| 4,641,653 A | 2/1987 | Rockey | 604/96 |
| 4,643,184 A | 2/1987 | Mobin-Udin | 128/345 |
| 4,647,416 A | 3/1987 | Seller, Jr. et al. | 264/118 |
| 4,649,922 A | 3/1987 | Wiktor | 128/344 |
| 4,650,446 A | 3/1987 | Luther | |
| 4,655,771 A | 4/1987 | Wallsten | 623/1 |
| 4,660,560 A | 4/1987 | Klein | 128/344 |
| 4,665,918 A | 5/1987 | Garza et al. | 128/343 |
| 4,676,241 A | 6/1987 | Webb et al. | 128/207 |
| 4,681,110 A | 7/1987 | Wiktor | 128/343 |
| 4,699,611 A | 10/1987 | Bowden | 604/1 |
| 4,705,517 A | 11/1987 | DiPisa, Jr. | 623/12 |
| 4,710,181 A | 12/1987 | Fuqua | 604/280 |
| 4,723,549 A | 2/1988 | Wholey et al. | 128/344 |
| 4,731,054 A | 3/1988 | Billeter et al. | 604/93 |
| 4,733,665 A | 3/1988 | Palmaz | 128/343 |
| 4,739,762 A | 4/1988 | Palmaz | 128/343 |
| 4,740,207 A | 4/1988 | Kreamer | 623/1 |
| 4,760,849 A | 8/1988 | Kropf et al. | 128/341 |
| 4,768,507 A | 9/1988 | Fischell et al. | 128/303 |
| 4,771,773 A | 9/1988 | Kropf | 128/303 |
| 4,776,337 A | 10/1988 | Palmaz | 128/343 |
| 4,787,899 A | 11/1988 | Lazarus | 623/1 |
| 4,842,575 A | 6/1989 | Hoffman, Jr. et al. | 600/36 |
| 4,848,343 A | 7/1989 | Wallsten et al. | 128/343 |
| 4,875,480 A | 10/1989 | Imbert | 128/343 |
| 4,878,906 A | 11/1989 | Lindemann et al. | 623/1 |
| 4,902,289 A | 2/1990 | Yannas | 623/1 |
| 4,923,464 A | 5/1990 | DiPisa, Jr. | |
| 4,954,126 A | 9/1990 | Wallsten | 600/36 |
| 4,994,032 A | 2/1991 | Sugiyama et al. | 604/96 |
| 4,998,539 A | 3/1991 | Delsanti | 128/898 |
| 4,998,923 A | 3/1991 | Samson et al. | 606/194 |
| 5,037,392 A | 8/1991 | Hillstead | 604/96 |
| 5,041,126 A | 8/1991 | Gianturco | 606/195 |
| 5,059,211 A | 10/1991 | Stack et al. | 606/198 |
| 5,061,275 A | 10/1991 | Wallsten et al. | 623/1 |
| 5,102,417 A | 4/1992 | Palmaz | |
| 5,104,399 A | 4/1992 | Lazarus | 623/1 |
| 5,192,307 A | 3/1993 | Wall | 623/1 |
| 5,195,984 A | 3/1993 | Schatz | |
| RE34,327 E | 7/1993 | Kreamer | 623/1 |
| 5,266,073 A | 11/1993 | Wall | 623/1 |
| 4,733,665 C1 | 1/1994 | Palmaz | 606/108 |
| 5,275,622 A | 1/1994 | Lazarus et al. | 623/1 |
| 5,306,286 A | 4/1994 | Stack et al. | 606/198 |
| 5,314,444 A | 5/1994 | Gianturco | 606/195 |
| 5,397,345 A | 3/1995 | Lazarus | 623/1 |
| 5,527,336 A | 6/1996 | Rosenbluth et al. | 606/192 |
| 5,562,728 A | 10/1996 | Lazarus et al. | 623/1 |
| 5,639,274 A * | 6/1997 | Fischell et al. | 606/108 |
| 5,662,700 A | 9/1997 | Lazarus | 623/1 |
| 5,669,936 A | 9/1997 | Lazarus | 623/1 |

FOREIGN PATENT DOCUMENTS

| | | |
|---|---|---|
| EP | 0 274 846 A1 | 12/1987 |
| EP | 0 282 175 A1 | 2/1988 |
| GB | 1 205 743 | 9/1970 |
| JP | 57-35985 | 9/1982 |
| SU | 0660689 | 5/1979 |
| SU | 660689 | 5/1979 |
| SU | 0764684 | 9/1980 |
| WO | WO 83/03752 | 4/1983 |

OTHER PUBLICATIONS

English Translation Of Certain Portions Of Nullity Action By Biotronik Against European Patent No. 0 221 570 (Appendix II, Exhibit Q).

Plea Of Invalidity Of European Patent No. 0 221 570 By Boston Scientific (Netherlands) (Sep. 12, 1997).

Memorandum Of Oral Pleading Filed On Behalf Of Boston Scientific (Netherlands) (Sep. 12, 1997).

Plea Notes Filed On Behalf Of Palmaz (Netherlands) Sep. 12, 1997).

Provisional Judgment Of District Court In The Hague (Netherlands) (Oct. 29, 1997).

Declaration of Lee P. Bendel.

Affidavit of Julio C. Palmaz.

Declaration of Marvin L. Woodall.

Expert Report of Dr. Nigel Pearson Buller.

"The Experimental Use of Steel Mesh Tubes for the Replacement of Arterial Segments", Lary et al., *AMA Archives of Surgery*, 72: 69–75, Jan. 1956.

"Transluminally–placed Coilspring Endarterial Tube Grafts", Dotter, et al., *Investigative Radiology*, 4: 329–332, Sep.–Oct. 1969.

Abstract of *Journal of Biomedical Materials Research*, 13(4), pp. 631–643, Jul. 1979.

*Dorland's Illustrated Medical Dictionary*, 26$^{th}$ Edition, pp. 675 and 759, 1981.

"Transluminal Expandable Nitinol Coil Stent Grafting: Preliminary Report", Dotter, et al., *Radiology*, 147: 259–60, Apr. 1983.

"Nonsurgical Placement of Arterial Endoprostheses: A New Technique Using Nitinol Wire", Cragg, et al., *Radiology*, 147: 261–63, Apr. 1983.

Abstract of *Journal of Orthodontistry*, 83(5), pp. 391–407, May 1983.

*Radiology*, 153P: 329, Program Abstract for the 1984 Annual Meeting of the Radiological Society of North America, Palmaz, et al., "Expandable Intraluminal Graft: A Preliminary Study", distributed to the public in Oct. 1984.

"Radiological Follow–up of Transluminally Inserted Vascular Endoprostheses: An Experimental Study Using Expanding Spirals", Maass, et al., *Radiology*, 152: 659–663, 1984.

"Percutaneous Endovascular Stents: An Experimental Evaluation", Wright, et al., *Radiology*, 156: 69–72, 1985.

"Expandable Intraluminal Graft: A preliminary Study", Palmaz, et al., *Radiology*, 156: 73–77, Jul. 1985; paper presented at 70$^{th}$ Scientific Assembly and Annual Meeting of the Radiological Society of North America, No. 25, 1984.

"Atherosclerotic Rabbit Aortas: Expandable Intraluminal Grafting", Palmaz, et al., *Radiology*, 160: 723–726, Sep. 1986.

"Flexible Balloon–expanded Stent for Small Vessels," Duprat, et al., *Radiology*, 162: 276–278, Jan. 1987.

Office Action dated Aug. 20, 1992 of 1$^{st}$ Reexam of '665 Patent.

Amendment dated Nov. 20, 1992 of 1$^{st}$ Reexam of '665 Patent.

Declaration of Julio C. Palmaz Under 37 C.F.R. § 1.131 dated Nov. 18, 1992 of 1$^{st}$ Reexam of '665 Patent.

Office Action dated Jan. 12, 1993 of 1$^{st}$ Rexxam of '665 Patent.

Amendment dated Mar. 12, 1993 of 1$^{st}$ Reexam of '665 Patent.

Testimony of Palmaz in *Windeler* dated Nov. 3, 1991, pp. 160–165.

Deposition of Palmaz in Cook Litigation dated Feb. 6, 1996, p. 968.

Deposition of Palmaz in Cook Litigation dated Feb. 6, 1996, p. 1000.

Deposition of Palmaz in Cook Litigation dated Apr. 16, 1996, p. 1122.

Deposition of Palmaz in Cook Litigation dated Dec. 5, 1996, p. 1805.

Deposition of Palmaz in Cook Litigation dated Dec. 5, 1996, p. 1850.

Deposition of Wholey in Cool Litigation dated Dec. 7, 1996, pp. 195–197.

Deposition of Wholey in Cook Litigation dated Dec. 7, 1996, p. 239.

Deposition of Wholey in Cook Litigation dated Dec. 7, 1996, p. 242.

Leewood Expert Report in Cook Litigation dated Jun. 17, 1997, pp. 6–7.

Cook Incorporated Catalog 1982–1984, Diagnostic & Interventional Products, pp. 65–66.

ASM Metals Reference Book, 2$^{nd}$ Ed., 1983, pp. 268–277.

Windeler Chart no date avail.

Natiella JR, Moresi JL, Flynn HE, Wirth JE, Baier RE, "Tissue Response to Surface–Treated Tantalum Implants: Preliminary Observations In Primates," J Biomed Mater Res, Jul. 1979, 13(4), pp. 631–643.

Cragg, AH, Lund G, Rysavy JA, Salomonowitz E, Castaneda–Zuniga WR, Amplatz K, "Precutaneous Arterial Grafting," Radiology Jan./1984, vol. 50, No. 1, pp. 45–49.

Palmaz JC, Sibbitt RR, Reuter SR, Tio EO, Rice WJ, "Expandable Intraluminal Graft: A Preliminary Sudy," Radiology, ul 1985, 156(1), pp. 73–77.

"Repositioning of Biliary Endoprosthesis with Gruntzig Balloon Catheters," EP Harries–Jones, S Fataar and EJ Tuft, *AJR* 138:771–772 (Apr. 1982).

"Effect of Maxillary Osteotomy on Subsequent Craniofacial Growth in Adolescent Monkeys," R. Nanda, J. Sugawara an RG Topazian, Am J Orthod (May 1983).

"Expandable Intraluminal Vascular Graft: A Feasibility Stidy," J. Palmaz, R. Sibbitt, F. Tio, S. Reuter, J. Peters, F. Garcia, *Surgery*, vol. 99, pp. 199–205 (Feb. 1986).

"Atherosclerotic Rabbit Aortas: Expandable Intraluminal Grafting", J. Palmaz, S. Windeler, F. Garcia, F. Tio, R. Sibbitt, S. Reuter, *Radiology*, vol. 160, pp. 723–726 (Sep. 1986).

*JACC*, vol. 9, No. 2, Abstracts p. 106A (Feb 1987).

"Intravascular Stents to Prevent Occulsion and Restenosis After Transluminal Angioplasty," U Sigward, J. Puel, V Mirkovitch, F Joffre and L Kappenberger, *N Engl J Med*, 316:701–6 (Mar. 19, 1987).

"Percutaneous Endovascular Graft: Experimental Evaluation," DD Lawrence, C Charnsangavej, KC Wright, C Gianturco and S Wallace, *Radiology*, 163:357–360 (May 1987).

"Self–Expanding Metallic Stents: Preliminary Evaluation in an Atherosclerotic Model," N Rollins, KC Wright, C Cjarnsangavej, S Wallace and C Gianturco, *Radiology*, vol. 163, No. 3, pp. 739–742 (Jun. 1987).

"Balloon–Expandable Intracoronary Stents in the Adult Dog," RA Schatz, JC Palmaz, FO Tio, F Garcia, O Garcia and SR Reuter, *Circulation*, vol. 76, No. 2, pp. 450–457 (Aug. 1987).

"Self–Expanding Endovascular Prosthesis: An Experimental Study," H Rosseau, J Puel, F Joffre, U Sigwart, C Duboucher, C Imbert, C Knight, L Kropf and H Wallsten, *Radiology*, 164:709–714 (Sep. 1987).

"Normal and Stenotic Renal Arteries: Experimental Balloon–Expandable Intraluminal Stenting," JC Palmaz, DT Kopp, H Hayashi, RA Schatz, G Hunter, FO Tio, O Garcia, R Alvarado, C Rees and SC Thomas, *Radiology*, 164:705–708 (Sep. 1987).

"Gianturco Expandable Wire Stents in the Treatment of Superior Vena Cava Syndrome Recurring After Maximum–Tolerance Radiation," J Rosch, JE Bedell, J Putnam, R Antonovic and B Uchida, *Cancer*, 60:1243–1246 (Sep. 15, 1987).

"One Year of Percutaneous Coronary Stenting, ", U Sigwart, C Imbert, A Essinger, A Fischer, H Sadeghi L Kappenberger, *Circulation*P II, vol. 76, No. 4 (Oct. 1987).

"Early and Late Results of Inracoronary Arterial Stenting After Coronary Angioplasty in Dogs," GS Roubin, KA Robinson, SB King, C Gianturco, AJ Black, JE Brown, RJ Siegel and JS Douglas, *Circulation*, vol. 76, No. 4, pp. 891–897 (Oct. 1987).

"Intravascular Stents to Prevent Restenosis After Transluminal Coronary Angioplasty," J Puel, H Rosseau, F Joffre, S Hatem, JM Fauvel, JP Bounhoure and CT Rangueil, *Circulation*, Pt. II, vol. 76, No. 4, 0105 (Oct. 1987).

"Abstracts From the 60th Scientific Sessions," *Circulation*, Pt. II, vol. 76, No. 4, IV–232 (Oct. 1987).

"Balloon Expandable Intra–Arterial Stents: Effect of Anticoagulation on Thrombus Formation," *Circulation*, JC Palmaz, OJ Garcia, DT Kopp, RA Schatz, FO Tio, and V Claravino, *Circulation*, Pt. II, vol. 76, No. 4 (Oct. 1987).

*J Cardiovasc. Surg.*, vol. 28, No. 5, pp. 39–41 (Sep.–Oct. 1987).

"Perkutan Implantierbare, Durch Ballon Aufdehnbare Gefässprothese," EP Strecker, P. Romaniuk, B. Schneider, M Westphal, E Zeitler, HRD Wolfund and N Freudenberg, *Disch Med Wschr*, 113:538–542 (1988).

"Modified Gianturco Expandable Wire Stents in Experimental and Clinical Use," J Rosch, JSE Putnam and BT Uchida, *Cirse, Porto Cervo*, vol. 31, No. 2, pp. 100–103 (1988).

"Implantation of Balloon–Expandable Intravascular Grafts by Catherization in Pulmonary Arteries and Systemic Veins," CE Mullins, MP O'Lauglin, GW Vick, DC Mayem RJ Myers, DL Kearney, RA Schatz and JC Palmaz, *Circulation*, vol. 77, No. 1, pp. 188–199 (1988).

"Modifications of Gianturco Expandable Wire Stents," BT Uchida, JS Putnam and J Rösch, *AJR*, 150:1185–1187 (May 1988).

Dotter, Charles T. and Judkins, Melvin P., "Transluminal Treatment of Arteriosclerosis Obstruction," Circulation 1964; 30:654–670 (C031558–575).

Rashkind W.J./, Miller, W.W.: Creation of an atrial septal defect without thoracotomy: A palliative approach to complete transposition of the great arteries. *JAMA*, 1966, 196; 991–92.

Peter Eichelter, MD, and Worthington G. Schenk, Jr.,MD Buffalo, "Prophylaxis of Pulmonary Embolism", *Arch Surg*—vol. 97, Aug. 1968, pp. 348–356.

James W. Pate, M.C., F.A.C.S., David Melvin, M.D., Richard C. Cheek, M.D., "A New Form of Vena Caval Interruption", *Annals of Surgery*, Jun. 1969, pp. 873–880.

Kazi Mobin–Uddin, MB, BS; Robert McLean; Hooshang Bolooki, MD; and James R. Jude, MD, Coral Gables, Fla., "Caval Interruption for Prevention of Pulmonary Embolism", *Arch Surg*/vol. 99, Dec. 1969.

James A. Hunter, M.D., Robert Sessions, Richard Buenger, M.D., "Experimental Balloon Obstruction of the Inferior Vena Cava", *Annals of Surgery*, Feb. 1970, pp. 315–320.

Lazar Greenfield, M.D., James R. McCurdy, M.D., Phillip P. Brown, M.D., and Ronald C. Elkins, M.D., Oklahoma City, Okla., :"A New Intracaval Filter Permitting Continued Flow and Resolution of Emboli", Apr., 1973, *Surgery*, vol. 73, No. 4, pp. 599–606.

Kazi Modin–Uddin, Joe R. Utley, and Lester R. Bryant, "The Inferior Vena Cava Umbrella Filter", *Progress in Cardiovascular Diseases*, vol. XVII, No. 5, (Mar./Apr.), 1975, pp. 391–399.

Goldstein et al., "Transcather Occlusion of Abdominal Tumors" *Radiology* 120: 539–545 (Sep. 1976) (C14058–65).

Morris Simon, M.D., Roy Kaplow, Ph.D., Edwin Salzman, M.D., and David Freiman, M.D., "A Vena Cava Filter Using Thermal Shape Memory Alloy", *Radiology*, 125: pp. 89–94, Oct. 1977.

The Surgical Experience and a One to Sixteen Year Follow–Up of 277 Abdominal Aortic Aneurysm. Gardner et al., American Journal of Surgery, 135, pp. 226–230 (1978).

Edwards, "Arterial Grafts" *Archives of Surgery*, 113: 1225–33 (Nov. 1978) (C14200–208).

Lunderquist et al., "Guidewire for Percutaneous Transheptic Cholangiography," *Radiology* 132: 228 (Jul. 1979) (C14114–15).

Campbell et al., "Expanded Microporous Polytetra Fluoroethylene as a Vascular Substitute: A two year Follow Up," *Surgery* 85: 177–78 (1979) (C14193–199).

Semb B.K.H., Tjonneland, S., Stake G., et al.: "Balloon valvotomy" of congenital pulmonary valve steonsis with tricuspid valve insufficiency. *Cardiovasc. Radial.*, 1979: 2:238–241.

Hoevels et al., "Percutaneous Transheptic Insertion of a Permanent Endoprosthesis in Obstructive Lesions of the Extrahepatic Bile Ducts," *Gastrointest. Radiol.* 4: 367–77 (1979) (C14402–13).

George E. Cimochowsky, M.D., Richard H. Evans, M.D., Christopher K. Zairins, M.D., Chien–Tai Lu, M.D., and Tom R. DeMeester, M.D., Chicago, Ill., "Greenfield Filter Versus Mobin–Uddin Umbrella", *J Thorac Cardiovac Surg*, 79: pp. 358–363, 1980.

Cope, "Balloon Dilatation of Closed Mesocaval Shunts," *AJR* 135: 989–993 (Nov. 1980) (C14337–41).

Dotter, Charles T., "International Radiology–Review of an Emerging Field," Seminars in Roentgenology, vol. XVI, No. 1 [Jan.] 1981 (C029209–210).

Smith et al., "Safe and Effective Catheter Angiography Through Prosthetic Vascular Grafts," *Radiology* 138: 487–88 (Feb. 1981) (C14216–17).

Fogarty, T.J.; Chin, A., Shoor, P.M., et al.: Adjunctive intraoperative arterial dilation: Simplified instrumentation technique. *Arch. Surg.* 1981, 116(11): 1391–8.

Harries–Jones et al., "Repositioning of Biliary Endoprosthesis with Grüntzig Balloon Catheters," *AJR* 138: 771–772 (Apr. 1982) (C13820–22).

Honickman et al., "Malpositioned Biliary Endoprosthesis; Retrieval Using a Vascular Balloon Catheter," *Radiology* 144: 423–425 (Jul. 1982) (C13817–19).

Ring et al. "A Simple, Indwelling Billary Endoprosthesis Made from Commonly Available Catheter Material" *AJR* 139: 615–617 (Sep. 1982) (C14054–57).

Aubrey M. Palestrant, M.D., Martin Prince, B.S., Morris Simon, M.D., "Comparative In Vitro Evaluation of the Nitinol Inferior Vena Cava Filter", *Radiology*: 145, pp. 351–355, Nov. 1982.

Kan, J.S., White R.I., Mitchell, S.E.: et al.: Percutaneous balloon valvuloplasty: A new method for treating congenital valve stenosis. *N. Eng J Med.*, 1982: 307:540–542.

Palmaz et al., "Removable Biliary Endoprosthesis," *AJR* 140: 812–814, Apr. 1983.

Coons et al., "Large–Bore, Long Biliary Endoprosthesis (Biliary Stents) for Improved Drainage," Radiology 148: 89–94 (Jul. 1983) (C13772–78).

Andrew Cragg, Gunnar Lund, Erich Salomonowitz, Joseph Rysavy, Flavio Castaneda, Wilfrido Castaneda–Zuniga, Kurt Amplatz, "A New Percutaneous Vena Cava Filter", *AJR* 141: pp. 601–604, Sep. 1983.

Karian Jr., et al., "A Simple Method for Insertion of Large Untapered Catheters" *AJR* 141: 792 (Oct. 1983) (C13808).

Teplick et al., "A New Biliary Endoprosthesis" *AJR* 141: 799–801 (Oct. 1983). (C14097–14100).

Castaneda–Zuniga, Ed. "Transluminal Angioplasty," 1983. (C14281–328).

Roehm, Jr., et al., "Percutaneous Transcatheter Filter for the Inferior Vena Cava", *Radiology*, vol. 150, No. 1, pp. 255–257 (Jan. 1984).

Andrew H. Cragg, M.D., Gunnar Lund, M.D., Joseph A Rysavy, B.A., Erich Salomonowitz, M.D., Wilfrido R. Castaneda–Zuniga, M.D., Kurt Amplatz, M.D., "Percutaneous Arerial Grafting", *Radiology*, vol. 150, No. 1, Jan. 1984, pp. 45–49. (C014108–113).

Kerlan, Jr. et al., "Biliary Endoprostheses, Insertion Using a Combined Peroral–Transhepatic Method," Radiology 1984; 150:828–830 (C14268–70).

Lund, et al., "A New Vena Caval Filter for Percutaneous Placement and Retrieval: Experimental Study", *Radiology*, vol. 152, No. 2, Aug. 1984, pp. 369–372.

Fogarty, T.J., Kinney, T.B.; Finn, J.C.: Current status of dilatation catheters and guiding instruments. *Am J. Cardiol.*, 1984, 15; 53(12): 97C–101C.

Fogarty, T.J.; Kinney, T.B., Intraoperative Coronary artery balloon–catheter dilatation. *Am. Heart J.* 1984, 107(4):845–51.

Fogarty et al., "Intraoperative Coronary Artery Balloon––Catheter Dilation," *American Heart Surgery* 107: 845–51 (1984) (C14209–15).

Labadibi Z., Wu, R.J., Walls, T.J.: Percutaneous balloon aortic valvuloplasty: Results in 23 patients. *Am. J. Cardioi.* 1984; 53; 194.

Inoue, K., Owani, T., Nahamura, T. Et el., Clinical application of transmitral commissurotomy by a new balloon cathether, *J. Thorac. Cardiovascular Surg.* 1984; 87:394.

Rolf W. Gunther, M.D., Hans Schild, M.D., Axel Fries, S. Storkel, M.D., "Vena Caval Filter to Prevent Pulmonary Embolism: Experimental Study", *Radiology*, vol. 156, No. 2, Aug. 1985, pp. 315–320.

Donald F. Denny, John J. Cronan, Gary S. Dorfman, Cordell Esplin, "Percutaneous Kimray–Greenfield Filter Placement by Femoral Vein Puncture", AJR 145: pp. 827–829, Oct. 1985.

Chusilp Charnangevej, M.D., Sidney Wallace, M.D., Kenneth C. Wright, Ph.D., Humberto Carrasco, M.D., Cesare Gianturco, M.D., "Endovascular Stent for Use in Aortic Dissection: An in Vitro Experiment", *Radiology* 1985: vol. 157, pp. 323–324.

Papanicolaou, et al. "Insertion of a Biliary Endoprosthesis Using a Balloon Dilatation Catheter," Gastrointest. Radiol. 10:394–96 (1985). (C013809–11).

Carrasco et al., "Expandable Biliary Endoprosthesis: An Experimental Study," *American Journal of Roentgenology*, 145 (1985), 1279–1281 (C013998–00).

Wallace et al, "Tracheobronchial Tree: Expandable Metallic Stents Used in Experimental and Clinical Applications," *Radiology* 1986; 158: 309–312 (Feb. 1986) (C13994–97).

Rosch et al., "Transjugular–Intraheptic Portacaval Shunt: An Experimental Work," *The American Journal of Surgery* 590–92 (C14575–77).

Kononov Discovery Deposition, Nov. 7–9, 17, 1996 (pp. 35–36, 41–43, 92–100, 122–125, 293–318, 455–457 redacted as confidential) (Appendix V, Exhibit P)(Kononov Notebook).

Kononov Evidentiary Deposition, Nov. 18–19, 1996 (Appendix V, Exhibit P)(Kononov Notebook).

Cook's Supplemental Responses to JJIS Discovery Request Nos. 15, 19, 20, 23, 24 and 39 (Appendix IV, Exhibit I) (Kononov Notebook).

Coons Supplemental Report, pp. 1–3 and Exhibits B–E thereto (Appendix VI, Exhibit M) (Kononov Notebook).

Coons Deposition, pp. 70–82 and 99–100 (Appendix V, Exhibit F) (Kononov Notebook).

Gardner Deposition, pp. 168–227, 232–257 (Appendix V, Exhibit K) (Kononov Notebook).

Palmaz Deposition, Dec. 5, 1996, pp. 1837–1860 (Appendix V, Exhibit AA) (Kononov Notebook).

Wholey Deposition, pp. 148–175 (Appendix V, Exhibit KK) (Kononov Notebook).

Criado Deposition, pp. 101–116 (Appendix V, Exhibit G) (Lazarus Notebook).

Kononov Discovery Deposition, Nov, 7, 1996, pp. 83–100 (pp. 92–100 redacted) (Appendix V, Exhibit P) (Lazarus Notebook).

Kononov Discovery Deposition, Nov. 9, 1996, pp. 458–470 (Appendex V, Exhibit P) (Lazarus Notebook).

Kononov Evidentiary Deposition, Nov. 18–19, 1996, pp. 126–142 (Appendix V, Exhibit P) (Lazarus Notebook).

Deposition testimony of Julius G. Hammerslag, May 11, 1996 (Appendix V, Exhibit M) (Hammerslag Notebook).

Cook's Supplemental Answers to JJIS' Discovery Request Nos. 6, 18–23, 34 and 37. Responses to request Nos. 19, 21, 22, 23 (Appendix IV, Exhibit F) (Hammerslag Notebook).

Cook's Supplemental Responses to JJIS' Discovery Request Nos. 18, 22 and 23. (Appendix IV, Exhibit H) (Hammerslag Notebook).

Adelman Report, pp. 4–8, 15–16. (Appendix VI, Exhibit A) (Hammerslag Notebook).

Coons Report, pp. 1, 6–7, 18–24, and Exhibits B–E thereto (Appendix VI, Exhibit L) (Hammerslag Notebook).

Coons Supplemental Report, pp. 2–3, and Exhibits B–E thereto (Appendix VI, Exhibit M) (Hammerslag Notebook).

Goolkasian Report, pp. 4, 13–18 (Appendix VI, Exhibit U) (Hammerslag Notebook).

Harmon Report, pp. 3–4, 26–27 (Appendix VI, Exhibit V) (Hammerslag Notebook).

Segal Answering Report, pp. 6–8, 10–11 (Appendix VI, Exhibit FF) (Hammerslag Notebook).

Wholey Report, pp. 5–7, 9–10 (Appendix VI, Exhibit KK) (Hammerslag Notebook).

Beck Deposition, pp. 216–228 (Appendix V, Exhibit A) (Hammerslag Notebook).

Buller Deposition, pp. 401–429 (Appendix V, Exhibit D) (Hammerslag Notebook).

Coons Deposition, pp. 83–84 (Appendix V, Exhibit F) (Hammerslag Notebook).

Emhardt Deposition, pp. 418–431 (Appendix V, Exhibit I) (Hammerslag Notebook).

Gardner Deposition, pp. 239–52, 339–376, 440–444 (Appendix V, Exhibit K) (Hammerslag Notebook).

Hodgson Deposition, pp. 79–88 (Appendix V, Exhibit N) (Hammerslag Notebook).

Kula Deposition, pp. 630–653, 647–651 (Appendix V, Exhibit Q) (Hammerslag Notebook).

Lipow Deposition, pp. 77–78, 114–177, 206–229, 273–344 (Appendix V, Exhibit U) (Hammerslag Notebook).

Palmaz Deposition, Feb. 6, 1996, pp. 919–923 (Appendix V, Exhibit AA) (Hammerslag Notebook).

Palmaz Deposition, Apr. 16, 1996, pp. 1089–1112, 1252–1271 (Appendix V, Exhibit AA) (Hammerslag Notebook).
Tobor Deposition, pp. 280–397 (Appendix V, Exhibit II) (Hammerslag Notebook).
Wholey Deposition, pp. 207–239 (Appendix V, Exhibit KK) (Hammerslag Notebook).
Gianturco U.S. Pat. No. 5,041,126 (Application No. 244, 669) (Appendix VIII, Exhibit B1) (Hammerslag Notebook).
Office Action, dated Oct. 2, 1989 in Application Ser. No. 244,669, p. 2 (Appendix VIII, Exhibit B2) (Hammerslag Notebook).
Jun. 29, 1994 Memorandum by Raymond Mehler (Appendix VIII, Exhibit A1) (Hammerslag Notebook).
Jul. 11, 1994 letter from H. Collins, Patent Counsel at Cordis to D. Latham, Medtronics (Appendix VIII, Exhibit A2) (Hammerslag Notebook).
Jul. 14, 1994 letter from D. Latham, Senior Patent Attorney at Medtronics to D. Hall, Cordis Corporation (Appendix VIII, Exhibit A3) (Hammerslag Notebook).
U.S. Pat. No. 4,969,458 (Appendix VIII, Exhibit C1) (Hammerslag Notebook).
Office Action in Application Ser. No. 69,636 dated Mar. 17, 1988, p. 3. (Appendix VIII, Exhibit C2) (Hammerslag Notebook).
Response to Office Action, p. 4–8 (Appendix VIII, Exhibit C3) (Hammerlag Notebook).
JJIS' Memorandum of Law on the Interpretation of the Asserted Claims of the '665 Patents pp. 4–5, 20–23 (Appendix VII, Exhibit A) (Ersek Notebook).
JJIS' Reply Memorandum of Law on the Interpretation of the Asserted Claims of the '665 Patent, pp. 30–33 (Appendix VII, Exhibit C) (Ersek Notebook).
Frenchick Deposition, JJIS 30(b)(6) witness on infringement, pp. 472–486 (Appendix V, Exhibit J) (Ersek Notebook).
Cook's Supplemental Responses to JJIS' Discovery Request Nos. 15, 19, 20, 23, 24 and 39, pp. 6–8 (Appendix IV, Exhibit I) (Ersek Notebook).
Adelman Report, pp. 7–8, 10–11, 16 (Appendix VI, Exhibit A) (Ersek Notebook).
Andros Report, entire document (Appendix VI, Exhibit B) (Ersek Notebook).
Collins Answering Report, entire document (Appendix VI, Exhibit J) (Ersek Notebook).
Coons Report, pp. 8, 18–24, Exhibits B–E (Appendix VI, Exhibit L) (Ersek Notebook).
Coons Supplemental Report, p. 3, Exhibits B–E (Appendix VI, Exhibit M) (Ersek Notebook).
Gardner Report, pp. 29–34 (Appendix VI, Exhibit S) (Ersek Notebook).
Goolkasian Report, pp. 2–3, 19–25, (Appendix VI, Exhibit U) (Ersek Notebook).
McIntosh Report, entire document (Appendix VI, Exhibit BB) (Ersek Notebook).
Segal Answering Report, pp. 6–8 (Appendix VI, Exhibit FF) (Ersek Notebook).
Wholey Report, pp. 6–10, 15–18 (Appendix VI, Exhibit KK) (Ersek Notebook).
Buller Deposition, pp. 354–360, 396–401 (Appendix V, Exhibit D) (Ersek Notebook).
Collins Deposition, pp. 59–95, 107–126 (Appendix V, Exhibit E) (Ersek Notebook).
Criado Deposition, Mar. 5, 1996, pp. 62–100, 126–143, 148–58, 170–172, 225–279 (Appendix V, Exhibit G) (Ersek Notebook).
Cumberland Deposition, pp. 25–27, 64–72 (Appendix V, Exhibit H) (Ersek Notebook).
Gardner Deposition, Dec. 18–19, 1996, pp. 162–170, 239–250, 429–440 (Appendix V, Exhibit K) (Ersek Notebook).
Hammerslag Deposition, pp. 74–75, 86–89 (Appendix V, Exhibit M) (Ersek Notebook).
Hodgson Deposition, Dec. 5, 1996, pp. 43–54, 57–78, 86–91, 112–163, 171–78, 188–211 (Appendix V, Exhibit N) (Ersek Notebook).
Kononov Discovery Deposition, Nov. 9, 1996, pp. 465–468 (Appendix V, Exhibit P) (Ersek Notebook).
Kononov Evidentiary Deposition, Nov. 18–19, 1996, pp. 92–96, 204–205, 208–224, 246–252 (Appendix V, Exhibit P) (Ersek Notebook).
Kula Deposition, Apr. 10, 1996, pp. 626–743 (Appendix V, Exhibit Q) (Ersek Notebook).
Leewood Deposition, pp. 63–77, 232–239, 241–246 (Appendix V, Exhibit S) (Ersek Notebook).
Lipow Deposition, Mar. 12, 1996, pp. 51–55, 120–122, 206–213 (Appendix V, Exhibit U) (Ersek Notebook).
Lipow Deposition, Mar. 13, 1996, pp. 374–386, 547–562 (Appendix V, Exhibit U) (Ersek Notebook).
Lipow Deposition, Mar. 14, 1996, pp. 572–605, 617–625, 643–644 (Appendix V, Exhibit U) (Ersek Notebook).
McIntosh Depositon, pp. 4–91, 103–197 (Appendix V, Exhibit V) (Ersek Notebook).
Palmaz Deposition, Apr. 16, 1996, pp. 1206–1232 (Appendix V, Exhibit AA) (Ersek Notebook).
Palmaz Deposition, Dec. 5, 1996, pp. 1777–1781 (Appendix V, Exhibit AA) (Ersek Notebook).
Palmaz Testimony, Dec. 5, 1991, pp. 11–24 (Appendix X, Exhibit B) (Ersek Notebook).
Palmaz Testimony, Dec. 6, 1991, pp. 32–63 (Appendix X, Exhibit B) (Ersek Notebook).
Tio Deposition, pp. 431–438 (Appendix V, Exhibit HH) (Ersek Notebook).
Tobor Deposition, Oct. 11, 1995, pp. 155–162, 189–236 (Appendix V, Exhibit II) (Ersek Notebook).
Tobor Deposition, May 1, 1996, pp. 684–723 (Appendix V, Exhibit II) (Ersek Notebook).
Tobor Deposition, Tobor, May 2, 1996, pp. 884–915 (Appendix V, Exhibit II) (Ersek Notebook).
Waller Deposition, pp. 32–33, 183–193, 206–244 (Appendix V, Exhibit JJ). (Ersek Notebook).
Wholey Deposition, Dec. 7, 1996, pp. 119–148, 175, 183–184 (Appendix V, Exhibit KK) (Ersek Notebook).
Windeler Testimony, Oct. 11, 1991, pp. 60–78, 99–103 (Appendix X, Exhibit C) (Ersek Notebook).
Affidavit of Erik K. Antonsson, Ph.D., P.E., C35148–84 (Appendix VIII, Exhibit G) (Ersek Notebook).
Petition to Reissue (Mar. 17, 1995) (Canada) (Appendix II, Exhibit K) (Ersek Notebook).
Decision of the Technical Board of Appeal (Apr. 2, 1996) (EPO) (Appendix II, Exhibit R) (Ersek Notebook).
Minutes of the Oral Proceedings (Apr. 2, 1996) (EPO) (Appendix II, Exhibit S) (Ersek Notebook).
Reply to Official Communication dated Oct. 6, 1989 (Jan. 31, 1990) (EPO) (Appendix II, Exhibit HH) (Ersek Notebook).

Amendment and Argument in Japanese Application No. 225376/91 (Dec. 11, 1996)(Appendix II, Exhibit MM) (Ersek Notebook).
Notification from Japanese Patent Office Regarding Document filed by Third Party to Reject Japanese Application No. 225376/91 (Aug. 20, 1996)(Appendix II, Exhibit OO) (Ersek Notebook).
Letter from John & Kernich requesting surrender of South African Patant No. 86/8414 (Aug. 5, 1996)(Appendix II, Exhibit UU) (Ersek Notebook).
Submission of New Claims (Mar. 19, 1990) (EPO) (Appendix II, Exhibit KKK) (Ersek Notebook).
Communication of European Search Report (Jul. 13, 1989) (Appendix II, Exhibit LLL) (Ersek Notebook).
Submission by Third Party to Japanese Patent Office (Jun. 14, 1996) (Appendix II, Exhibit MMM) (Ersek Notebook).
Response to May 13, 1994 Communication (Nov. 4, 1994) (EPO) (Appendix II, Exhibit QQQ) (Ersek Notebook).
Communication (May 13, 1994) (EPO) (Appendix II, Exhibit RRR) (Ersek Notebook).
Response to Second Official Report (Oct. 19, 1994) (Australia) (Appendix II, Exhibit TTT) (Ersek Notebook).
Second Official Report (Mar. 10, 1994) (Australia) (Appendix II, Exhibit UUU) (Ersek Notebook).
Response to First Official Report (Feb. 22, 1994) (Australia) (Appendix II, Exhibit VVV) (Ersek Notebook).
First Official Report (Feb. 23, 1993) (Australia) (Appendix II, Exhibit WWW) (Ersek Notebook).
Response to Official Report (Sep. 5, 1996) (Australia) (Appendix II, Exhibit YYY) (Ersek Notebook).
Official Report (Feb. 19, 1996) (Australia) (Appendix II, Exhibit ZZZ) (Ersek Notebook).
Statements Submitted to EPO by Opposer (Mar. 18, 1996) (Appendix II, Exhibit T) (Ersek Notebook).
Notice of Issues to be Addressed at Oral Proceedings (Feb. 27, 1996) (EPO) (Appendix II, Exhibit U) (Ersek Notebook).
Brief Submitted by Opposer (Jan. 18, 1996) (EPO) (Appendix II, Exhibit V) (Ersek Notebook).
Patentee Submission of Amended Claims and Statement of Arguments (Jan. 20, 1995) (EPO) (Appendix II, Exhibit W) (Ersek Notebook).
Brief Submitted by Opposer (Jul. 11, 1995) (EPO) (Appendix II, Exhibit X) (Ersek Notebook).
Statement of Grounds of Appeal (Nov. 22, 1993) (EPO) (Appendix II, Exhibit Y) (Ersek Notebook).
Revocation of European Patent (Jul. 12, 1993) (EPO) (Appendix II, Exhibit Z) (Ersek Notebook).
Brief Submitted by Opposer (May 17, 1993) (EPO) (Appendix II, Exhibit AA) (Ersek Notebook).
Response to Official Communication dated Nov. 8, 1991 (EPO) (Aug. 17, 1992) (Appendix II, Exhibit BB) (Ersek Notebook).
Notice to Opposition by Advanced Surgical Intervention Inc. (Oct. 30, 1991) (EPO) (Appendix II, Exhibit CC) (Ersek Notebook).
Notice of Opposition by Boston Scientific Corp. (Jan. 30, 1991) (EPO) (Appendix II, Exhibit DD) (Ersek Notebook).
Translation of Submission by Third Party Trial–Demanding Brief (Nov. 8, 1996) (Japan) (Appendix II, Exhibit NN) (Ersek Notebook).
Patrick W. Serruys, Rotterdam Thoraxcentre Interventional Cardiology Group, Handbook of Coronary Stents, 1997.

Brief of Terumo Kobushiki Kaisha to Invalidate Patent, Nov. 8, 1996 (Appendix II, Exhibit AAAA) (Ersek Notebook).
Reply to Patent Opposition and Request for Amendment, Sep. 25, 1997 (Appendix II, Exhibit BBBB) (Ersek Notebook).
Arterial Vascular Engineering, Inc.'s "Complaint For Declaratory Relief of Patent Invalidity, Unenforceability, Noninfringement, and For Antitrust Violations", Case No. 97–700, Dec. 26, 1997.
Cordis Corporations's "Complaint For Patent Infringement and Demand for Jury Trial", Case No. 97–550, Oct. 3, 1997.
Cordis Corporation's "First Amended Complaint and Demand for Jury Trial", Case No. 97–550–SLR, Oct. 21, 1997.
Boston Scientific Corporation and SCIMED Life Systems, Inc.'s "Answer", Case No. 97–550–SLR, Nov. 12, 1997.
Cordis Corporation's "Cordis' Motion for a Preliminary Injunction Against Arterial Vascular Engineering, Inc.", Case No. 97–550–SLR, Dec. 29, 1997.
Cordis Corporation's "Cordis Corporation's Motion For a Preliminary Injunction", Case No. 97–550, Oct. 8, 1997.
Arterial Vascular Engineering, Inc's First Amended Complaint For Declaratory Relief of Patent Invalidity, Unenforceability, Noninfringement, and For Antitrust Violations, Jan. 27, 1998, Arterial Vascular Engineering, Inc. v. Cordis Corporation, Johnson & Johnson and Expandable Grafts Partnership, Civil Action No. 97–700.
Cordis Corporation and Expandable Grafts Partnership's "Complaint and Demand for Jury Trial", Feb. 6, 1998, Cordis Corporation and Expandable Grafts Partnership v. Advanced Cardiovascular Systems, Inc., Guidant Corporation, Arterial Vascular Engineering, inc. Boston Scientific Corporation and SCIMED Life Systems, Inc. Delaware District Court Case No. 98–65.
Cordis Corporation's "Motion to Amend Complaint and to Add a Party", Feb. 6, 1998, Cordis Corporation v. Advanced Cardiovascular Systems, Inc., Guidant Corporation, Arterial Vascular Engineering, Inc., Boston Scientific Corporation and SCIMED Life Systems, Inc., Delaware District Court Case No. 97–550–SLR.
Cordis Corporation's "Motion for Consolidation Pursuant to Rule 42(a)", Feb. 6, 1998, Cordis Corporation v. Advanced Cardiovascular Systems, Inc. Guidant Corporation, Arterial Vascular Engineering, Inc., Boston Scientific Corporation and SCIMED Life Systems, Inc., Delaware District Court Case No. 97–550–SLR, and Cordis Corporation and Expandable Grafts Partnership v. Advanced Cardiovascular Systems, Inc., Guidant Corporation, Arterial Vascular Engineering, Inc. Boston Scientific Corporation and SCIMED Life Systems, Inc. Delaware District Court Case No. 98–65.
Arterial Vascular Engineering, Inc.'s "Answer and Counterclaim", Feb. 27, 1998, Arterial Vascular Engineering, Inc. v. Cordis Corporation et al., Delaware District court Case No. 97–550–SLR.
Expandable Grafts Partnership's "Answer to Arterial Vascular Engineering, Inc.'s First Amended Complaint and Counterclaim", Jul. 27, 1998, Arterial Vascular Engineering, Inc. v. Cordis Corporation et al., Delaware District Court Case No. 97–700–SLR.
Reply of Plaintiff Arterial Vascular Engineering, Inc, to Counterclaims of Defendant Cordis Corporation (Mar. 31, 1998), Arterial Vascular Engineering, Inc. v. Cordis Corporation et al., Delaware District Court Case No. 97–700–SLR.

Reply of Plaintiff Arterial Vascular Engineering, Inc. to Counterclaims Expandable Grafts Partnership, (Mar. 31, 1998) Arterial Vascular Engineering, Inc. v. Cordis Corporation et al., Delaware District Court Case No. 97–700–SLR.

Answer and Counterclaims of Defendant Advanced Cardiovascular Systems, Inc., (Apr. 9, 1998), Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc., Delaware District Court Civil Action No. 97–550–SLR (Consolidated).

Boston Scientific Corporation and SCIMED Life Systems, Inc.'s Answer to the Second Amended Complaint in Case No. 97–550 and to the identical Complaint Assigned Case No. 98–65 (Apr. 15, 1998), Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc., Delaware District Court Civil Action No. 97–550–SLR.

Expandable Grafts Partnership's Answers and Objections to AVE's First Set of Interrogatories (Apr. 22, 1998), Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc., Delaware District Court Civil Action No. 97–550–SLR.

Defendant Arterial Vascular Engineering, Inc.'s Responses to Plaintiff's First Set of Interrogatories Nos. 1–13 (Apr. 28, 1998), Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc., Delaware District Court Civil Action No. 97–550–SLR.

Advanced Cardiovascular Systems, Inc. and Guidant Corporation's First Supplemental Response to Plaintiff's First Set of Interrogatories (No. 11)(Feb. 3, 1998), Cordis Corporation v. Advanced Cardiovascular Systems, Inc., Guidant Corporation, Arterial Vascular Engineering, Inc., Boston Scientific Corporaton and SCIMED Life Systems, Inc., Delaware District Court Civil Action No. 97–550–SLR.

Boston's Skeleton Argument (undated), Boston Scientific Limited and Boston Scientific International B.V. v. Expandable Grafts Partnership and Boston Scientific Limited and Boston Scientific International B.V. v. Julio C. Palmaz, High Court of Justice, Chancery Division, Patents Court.

Skeleton Argument of Palmaz/EGP (undated), Boston Scientific Limited and Boston Scientific International B.V. v. Julio C. Palmaz and Expandable Grafts Partnership, High Court of Justice, Chancery Division, Patents Court.

Boston's Closing Submissions (undated), Boston Scientific Limited and Boston Scientific International B.V. v. Expandable Grafts Partnership and Boston Scientific Limited and Boston Scientific International B.V. v. Julio C. Palmaz, High Court of Justice, Chancery Division, Patents Court.

EGP's Final Submissions (undated), Boston Scientific Limited and Boston Scientific International B.V. v. Julio C. Palmaz and Expandable Grafts Partnership, High Court of Justice, Chancery Division, Patents Court.

Judgment (Jun. 26, 1998), Boston Scientific Limited and Boston Scientific International B.V. v. Julio C. Palmaz and Expandable Grafts Partnership, High Court of Justice, Chancery Division, Patents Court.

Affidavit of Dr. Julio C. Palmaz (Dec. 5, 1997), Boston Scientific Limited and Boston Scientific International B.V. v. Julio C. Palmaz, High Court of Justice, Chancery Division, Patents Court.

Affidavit of Ben D. Tobor (Dec. 8, 1997), Boston Scientific Limited and Boston Scientific International B.V. v. Julio C. Palmaz, High Court of Justice, Chancery Division, Patents Court.

Affidavit of Martin Aufenanger (Dec. 8, 1997), Boston Scientific Limited and Boston Scientific International B.V. v. Julio C. Palmaz, High Court of Justice, Chancery Division, Patents Court.

Deposition of Nigel P. Buller, M.D. (Dec. 20, 1997), Cordis Corporation v. Advanced Cardiovascular Systems, District Court of Delaware Case No. 97–550.

Deposition of Alfred Steward Windeler, Ph.D. (Jan. 28, 1998), Cordis Corporation v. Advanced Cardiovascular Systems, District Court of Delaware Case No. 97–550.

Deposition of Richard A. Bowman (Jan. 9, 1998), Cordis Corporation v. Advanced Cardiovascular Systems, District Court of Delaware Case No. 97–550.

Deposition of Gary Schneiderman (Jan. 16, 1998), Cordis Corporation v. Advanced Cardiovascular Systems, District Court of Delaware Case No. 97–550.

Deposition of Julio Cesar Palmaz (Dec. 29, 1997), Cordis Corporation v. Advanced Cardiovascular Systems, District Court of Delaware Case No. 97–550.

Program Abstract for the 1984 Annual Meeting of the Radiological Society of North America: Palmaz et al., "Expandable Introluminal Graft: A Preliminary Study" distributed to the public Oct. 1984.

Letter of Counsel for Cook to Counsel for Patent Owner dated Jan. 17, 2000, and accompanying 30 page attachment.

Letter of Counsel for Patent Owner to Counsel for Cook dated Feb. 7, 2000.

Advanced Cardiovascular Systems, Inc. and Guidant Corp.'s Objections and Responses to Plaintiff's First Set of Interrogatories (Nos. 1–13)(Dec. 2, 1997), Cordis Corporation et al. v. Advanced Cardiovascular systems, Inc. et al., Case No. 97–550–SLR (Consolidated).

Boston Scientific Corporation and SCIMED Life Systems Inc's Amended Objections and Responses to Cordis Corporation's First Set of Interrogatories (Nov. 16, 1999), Cordis Corporation and Expandable Grafts Partnership v. Advanced Cardiovascular Systems, Inc. et al., Case No. 97–550–SLR (Consolidated).

Boston Scientific Corporation and SCIMED Life Systems, Inc.'s Second Amended Objections and Supplemental Responses to Cordis Corporation's First Set of Interrogatories(Nos. 4–11)(Jan. 14, 2000), Cordis Corporation and Expandable Grafts Partnership v. Advanced Cardiovascular Systems, Inc. et al., Case No. 97–550–SLR (Consolidated).

Boston Scientific Corporation and SCIMED Life Systems, Inc. Response to Plaintiff's Third Set of Interrogatories(Jan. 14, 2000), Cordis Corporation et al., v. Advanced Cardiovascular Systems, Inc. et al., Case No. 97–550–SLR (Consolidated).

Medtronic Ave, Inc.'s Objections and Responses to Plaintiff Cordis Corporation's Third Set of Interrogatories Nos. 16–27 (Dec. 9, 1999), Cordis Corporation et al., v. Advanced Cardiovascular, Inc.'s et al., Case No. 97–550–SLR (Consolidated).

Medtronic Ave, Inc.'s First Amended Objections and Supplemental Responses to Plaintiff's First Set of Interrogatories Nos. 1–13 (Dec. 9, 1999), Cordis Corporation et al., v. Advanced Cardiovascular Systems, Inc. et al., Case No. 97–550–SLR (Consolidated).

Expandable Grafts Partnership's Response to Boston Scientific Corporation and SCIMED Life Systems, Inc.'s First Set of Requests for Admission directed to Expandable Grafts Partnership (Jan. 19, 2000), Cordis Corporation and Expandable Grafts Partnership v. Advanced Cardiovascular Systems, Inc. et al., Case No. 97–550–SLR (Consolidated).

Expandable Grafts Partnership Responses to Advanced Cardiovascular Systems, Inc., Medtronic Ave, Inc., Boston Scientific Corporation and SCIMED Life Systems, Inc.'s Joint Requests for Admissions to Expandable Grafts Partnership (Nos. 1–31), (Jan. 19, 2000), Cordis Corporation et al.,v. Advanced Cardiovascular Systems, Inc. et al., Case No. 97–550–SLR (Consolidated).

Plaintiff Cordis Corporation's Response to Joint Interrogatories (Nos. 1–25) of Defendants Advanced Cardiovascular Systems, Inc., Guidant Corporation, Medtronic Ave, Inc. Boston Scientific Corporation and SCIMED Life Systems, Inc. (Jan. 10, 2000), Cordis Corporation et al., v. Advanced Cardiovascular Systems, Inc., et al., Case No. 97–550–SLR (Consolidated).

Cordis Corporation's Objections and Responses to Medtronic Ave's Requests for Admission (Jan. 10, 2000), Cordis Corporation et al., v. Advanced Cardiovascular Systems, Inc. et al., Case No. 97–550–SLR (Consolidated).

Plaintiff Cordis Corporations's Objections and Responses to Defendant Advanced Cardiovascular Systems, Inc.'s Third Set of Interrogatories to Plaintiff Cordis Corporation (Nos. 13–35) (Jan. 10, 2000), Cordis Corporation et al., v. Advanced Cardiovascular Systems, Inc., Case No. 97–50–SLR (Consolidated).

John P. Milnamow Deposition and exhibits, Oct. 27 (vol. 1), Oct. 28 (vol. 2), Oct. 29 (vol. 3) 1999, and John P. Milnamow 30 (b)(6) Deposition, Oct. 29, 1999, Cordis Corporation et al., v. Advanced Cardiovascular Systems, Inc. et al., Case No. 97–550–SLR (Consolidated).

Jason Lipow Deposition and exhibits, May 4, 1999 (vol. 1), and May 5, 1999 (vol. 2), Cordis Corporation et al., v. Advanced Cardiovascular System, Inc. et al., Case No. 97–550–SLR (Consolidated).

Joel E. Siegel Deposition and exhibits, Dec. 7, 1999, Cordis Corporation et al., v. Advanced Cardiovascular Systems, Inc. et al., Case No. 97–550–SLR (Consolidated).

Stanton Rowe Deposition and exhibits, Nov. 11, 1999, Cordis Corporation et al.,v. Advanced Cardiovascular Systems, Inc. et al., Case No. 97–550–SLR (Consolidated).

Frank J. Criado, M.D. Deposition and exhibits, Nov. 23, 1999, Cordis Corporation et al., v. Advanced Cardiovascular Systems, Inc. et al., Case No. 97–550–SLR (Consolidated).

Ben D. Tobor Deposition and exhibits, Jun.14–8 (vols. 1–5) and Dec. 3, 1999, Cordis Corporation et al., v. Advanced Cardiovascular Systems, Inc., et al., Case No. 97–550–SLR (Consolidated).

John Kula Deposition and exhibits, Apr. 20 & 21, 1999 and Nov. 16–18, 1999, Cordis Corporation et al., v. Advanced Cardiovascular Systems, Inc. et al., Case No. 97–550–SLR (Consolidated).

Julio C. Palmaz, MD, Deposition and exhibits, Jul. 26–30, 1999, Aug. 30–Sep. 3, 1999, Oct. 14–16, 1999, Jan. 20, 2000, Cordis Corporation et al., v. Advanced Cardiovascular Systems, Inc., et al, Case No. 97–550–SLR (Consolidated).

George Andros, MD, Deposition and exhibits, Dec. 14, 1999, Cordis Corporation et al., v. Advanced Cardiovascular Systems, Inc., et al, Case No. 97–550–SLR (Consolidated).

Amendment Statement of Claim, Sep. 29, 1999, Johnson & Johnson, Inc. Expandable Grafts Partnership and Cordis Corporation (plantiff's) and Arterial Vascular Engineering Canada, Inc., (defendant), Court File No. T–808–98, Federal Court of Canada—Trial Division.

Amendment Statement of Claim, Sep. 29, 1999, Johnson & Johnson, Inc., Expandable Grafts Partnership and Cordis Corporation (plantiff's) and Boston Scientific Ltd/Boston Scientifique Ltee, (defendant), Court File No. T–1822–97, Federal Court of Canada—Trial Division.

Amendment Statement of Claim, Sep. 29, 1999, Johnson & Johnson, Inc., Expandable Grafts Partnership and Cordis Corporation (plaintiff's) and Guidant Canada Corporation (defendant), Court File No. T–1836–97, Federal Court of Canada—Trial Division.

Boston Scientific Medizintechnik GmbH's Response (dated Aug. 30, 1999) to the defendant in the Nullity Action's substantiation of its Appeal of Feb. 12, 1999, Boston Scientific Medizintechnik GmbH (plaintiff in the nullity action) v. Expandable Grafts Partnership (defendant in the nullity action), The Federal Court of Justice, Herrenstrasse 45a, in re: EP 335,341.

Amended Statement of Defence filed on behalf of Guidant Canada Corp., Oct. 25, 1999, Johnson & Johnson, Inc., Expandable Grafts Partnership and Cordis Corporation (plaintiff's) and Guidant Canada Corporation (defendants), Court File No. T–1836–97, Federal Court of Canada—Trial Division.

Twice Amended Statement of Defence and Counterclaim, Oct. 28, 1999, Johnson & Johnson, Inc. Expandable Grafts Partnership and Cordis Corporation (plaintiff's) and Boston Scientific Ltd./Boston Scientifque Ltee (defendant), Court File No. T–1822–97, Federal Court of Canada—Trial Division.

Defendant's First Pleading, Jun. 29, 1999, Terumo Kabushiki Kaisha v. Expandable Grafts Partnership, Heisei 10(Gyo–ke) No. 354, Tokyo High Court, Civil Section No. 18.

Plaintiff's Pleading (2), Sep. 16, 1999, Terumo Kabusihki Kaisha v. Expandable Grafts Partnership, Heisei 10(Gyo–ke) No. 354, Tokyo High Court, Civil Section No. 18.

Amended Statement of Defence and Counterclaim of Arterial Vascular Engineering Canada Inc., Oct. 29, 1999, Johnson & Johnson, Inc., Expandable Grafts Partnership and Cordis Corporation (plaintiff's) and Arterial Vascular Engineering Canada, Inc., Case File No. T–808–98, Federal Court of Canada—Trial Division.

Plaintiff Cordis Corporation's Claim Charts in re: U.S. Pat. No. 4,739,762, Cordis Corporation et al., v. Advanced Cardiovascular Systems, Inc., et al., Case No. 97–550–SLR (Consolidated).

Defendant Boston Scientific's Claim Charts in re: U.S. Pat. No. 4,739,762 dated, Cordis Corporation et al., v. Advanced Cardiovascular Systems, Inc., et al., Case No. 97–550–SLR (Consolidated).

Defendant Medtronic AVE's Claim Charts in re: U.S. Pat. No. 4,739,762 dated , Cordis Corporation et al., v. Advanced Cardiovascular Systems, Inc., et al., Case No. 97–550–SLR (Consolidated).

Betty Rohr Deposition, Oct. 6, 1999, Cordis Corporation et al., v. Advanced Cardiovascular Systems, Inc., et al., Case No. 97–550–SLR (Consolidated).

Reply Brief in Support of Cordis' Motion for Reargument of this Court's Decisions dated Jun. 18, 1999 on "Slots Formed Therein", Aug. 3, 1999, Cordis Corporation et al., v. Advanced Cardiovascular Systems, Inc., et al, Case No. 97–550–SLR (Consolidated).

Memorandum of Medtronic Ave, Inc. in Opposition to Cordis Corporation's Motion for Reargument of the Court's Jun. 18, 1999, Memorandum Opinion, Order and Memorandum Order, Jul. 26, 1999, Cordis Corporation et al., v. Advanced Cardiovascular Systems, Inc., et al, Case No. 97–550–SLR (Consolidated).

Judgements in the Joint Actions with Docket No. 97/1367, Julio C. Palmaz, et al, v. Boston Scientific B.V., et al., and Docket No. 97/1606, Boston Scientific International B.V., et al., v. Julio C. Palmaz, et al, dated Jun. 23, 1999, The Hague District Court, Civil Law Division –Chamber D.

Memorandum Opinion of Jan. 15, 1999 by District Judge Sue L. Robinson, Cordis Corporation, et al., v. Advanced Cardiovascular Systems, Inc., et al, Case No. 97–550–SLR (Consolidated).

Third Amended Complaint and Demand for Jury Trial, Jun. 1, 1999, Cordis Corporation, et al., v. Advanced Cardiovascular Systems, Inc., et al., Case No. 97–550–SLR (Consolidated).

Answer and Counterclaim to the Third Amended Complaint and Demand for Jury Trial, Jun. 13, 1999, Cordis Corporation, et al, v. Advanced Cardiovascular Systems, Inc., et al, Case No. 97–550–SLR (Consolidated).

Amended Answer and Counterclaims of Defendant Medtronic Ave, Inc. to Third Amended Complaint of Plaintiff Cordis Corporation, Jun. 28, 1999, Cordis Corporation, et al, v. Advanced Cardiovascular Systems, Inc., et al, Case No. 97–550–SLR (Consolidated).

Answer and counterclaim of defendant Advanced Cardiovascular Systems, Inc., Jun. 15, 1999, Cordis Corporation, et al.v. Advanced Cardiovascular Systems, Inc., et al., Case No. 97–550–SLR.

Answer of Defendant Guidant Corporation, Jun. 15, 1999, Cordis Corporation, et al., v. Advanced Cardiovascular Systems, Inc., et al., Case No. 97–550–SLR.

Reply to Counterclaim of Defendant Advanced Cardiovascular Systems, Inc., Jul. 6, 1999, Cordis Corporation, et al., v. Advanced Cardiovascular Systems, Inc., Case No. 97–550–SLR.

Reply to Counterclaim of Defendants Boston Scientific and SCIMED, Jul 6, 1999, Cordis Corporation, et al., v. Advanced Cardiovascular Systems, Inc., Case No. 97–550–SLR.

Reply to Counterclaim of Defendants Boston Scientific and SCIMED, Jul. 6, 1999, Cordis Corporation, et al., v. Advanced Cardiovascular Systems, In c., Case No. 97–550–SLR.

Memorandum Order of Jun. 18, 1999, Cordis Corporation, et al., v. Advanced Cardiovascular Systems, Inc., v. Advanced Cardiovascular Systems, Inc., Case No. 97–550–SLR.

Order of Jun. 18, 1999, Cordis Corporation, et al, v. Advanced Cardiovascular Systems, Inc., et al., Case No. 97–550–SLR.

Richard A. Schatz, M.D. Deposition, Jul. 12–16, 1999, and Dec. 2, 19999, Cordis Corporation et al, v. Advanced Cardiovascular Systems, Inc. et al, Case No. 97–550–SLR.

Expert Witness Report of John F. Witherspoon filed by Boston Scientific Corporation et al., Jan. 24, 2000, Cordis Corporation et al., v. Advanced Cardiovascular Systems, Inc. et al., Case No. 97–550–SLR (Consolidated).

Expert Report of Dr. Andrew S. Douglas filed by Boston Scientific Corporation et al., Jan. 24, 2000, Cordis Corporation, et al., v. Advanced Cardiovascular Systems, Inc. et al., Case No. 97–550–SLR (Consolidated).

Expert Report of David C. Cumberland, M.D., filed by Boston Scientific Corporation et al., Jan. 24, 2000, Cordis Corporation, et al., v. Advanced Cardiovascular Systems, Inc., Case No. 97–550–SLR (Consolidated).

Rebuttal Expert Report of Howard Hermann, M.D., dated Feb. 28, 2000, Cordis Corporation, et al. vs. Advanced Cardiovascular Systems, Inc., et al., Case No. 97–550–SLR (Consolidated).

Rebuttal Expert Report of Nigel Buller, B.Sc., M.B., F.R.C.P., dated Feb. 2000, Cordis Corporation, et al. vs Advanced Cardiovascular Systems, Inc., et al., Case No. 97–550–SLR (Consolidated).

Rebuttal Expert Report of George Andros, M.D., dated Feb. 28, 2000, Cordis Corporation, et al. vs. Advanced Cardiovascular Systems, Inc., et al., Case No. 97–550–SLR (Consolidated).

Rebuttal Expert Report of John M. Collins, Ph.D.., dated Feb. 28, 2000, Cordis Corporation, et al. vs. Advanced Cardiovascular Systems, Inc., et al., Case No. 97–550–SLR (Consolidated).

Rebuttal Expert Report of Lee P. Bendel, dated Feb. 28, 2000, Cordis Corporation, et al., vs. Advanced Cardiovascular Systems, Inc., et al., Case No. 97–550–SLR (Consolidated).

Expert Report of John T. Goolkasian, Esquire pursuant to rule 26(a)(2)(B), FED. R. CIV. P., Cordis Corporation et al., vs. Advanced Cardiovascular Systems, Inc., et al., Case No. 97–550–SLR (Consolidated).

Rebuttal Expert Report of David C. Cumberland, M.D., dated Feb. 28, 2000, Cordis Corporation, et al., vs. Advanced Cordiovascular Systems, Inc., et al., Case No. 97–550–SLR (Consolidated).

Answering Report of Dr. Rodney S. Badger on behalf of Medtronic Ave, Inc., dated Feb. 29, 2000, Cordis Corporation, et al. vs. Advanced Cardiovascular Systems, Inc., et al., Case No. 97–550–SLR (Consolidated).

Rebuttal Expert Report of Dr. Andrew S. Douglas, dated Mar. 2000, Cordis Corporation, et al., vs Advanced Corporation Systems, Inc., et al., Case No. 97–550–SLR (Consolidated).

Rebuttal Expert Report of Alan J. Snyder, Ph.D., dated Mar. 1, 2000, Cordis Corporation, et al., vs Advanced Corporation Systems, Inc., et al., Case No. 97–550–SLR (Consolidated).

(Abstract) Work in Progress—General Diagnosis. "Expandable Intraluminal Graft: A Preliminary Study," Palmaz, et al. presented at the 70th Scientific Assembly and Annual Meeting of the Radiological Society of North American, Nov. 25–30, 1984.

Office Action of Aug. 20, 1992 (First Reexamination).

Office Action of Jul. 30, 1999 (Second Reexamination).
Patent Owner's Amendment of Jul. 30, 1999.
Declaration of George Andros M.D.
Cook's Request for Reexamination, Feb. 13, 1998.
"Expandable Intraluminal Graft: A Preliminary Study—Work in Progress," by Palmaz, et al., *Radiology*, 156: 73–77, Jul. 1985.
The Radial Expansion of the P204 and PS1540 Stents, Alan R. Leewood, Ph.D., Jun. 18, 1996.
A Supplemental Report on Radial Expansion of the JJIS P308 Stent, by Alan R. Leewood, Ph.D. et al., Nov. 4, 1996.
Nov. 5, 1991 Testimony of Palmaz in *Windeler*, p. 160–161; 162–165.
Nov. 25, 1991 Testimony of Kula in *Windeler*, p. 14.
Dec. 6, 1991 Testimony of Palmaz in *Windeler*, p. 48; 62–63.
Oct. 27, 1995 Deposition of Kula, p. 172–173; 204.
Nov. 16, 1995 Deposition of Shaknovich, p. 93–98; 99–100; 126–127.
Jan. 5, 1996 Deposition of Goldberg, p. 55; 122–125; 236; 281; 283.
Apr. 10, 1996 Deposition of Kula, p. 604–607; 711–712; 719–723; 726–727.
Apr. 16, 1996 Deposition of Palmaz, p. 1141–1142; 1183.
May 15, 1996 Deposition of Schatz, p. 95–96; 144; 187–188.
May 16, 1996 Deposition of Schatz, p. 447–448; 565.
May 17, 1996 Deposition of Tio, p. 311; 314; 320–322; 347.
Dec. 5, 1996 Deposition of Palmaz, p. 1805–1806.
Dec. 7, 1996 Deposition of Wholey, p. 59–60; 102–105; 155; 175.
Dec. 13, 1996 Deposition of Buller, p. 35–38.

* cited by examiner

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 13–28 is confirmed.

Claims 1 and 7 are determined to be patentable as amended.

Claims 2–6, 8–12 and 29–32, dependent on an amended claim, are determined to be patentable.

New claims 33 and 34 are added and determined to be patentable.

1. A method for implanting a prosthesis at a desired location within a body passageway comprising the steps of:
   disposing the prosthesis upon a catheter;
   inserting the prosthesis and catheter within the body passageway by catheterization of said body passageway;
   delivering the catheter and prosthesis through the body passageway to the desired location in the body passageway without surgically exposing the desired location of the body passageway, *wherein the desired location in the body passageway is the location of an existing natural obstruction*; and
   providing controllable expansion of the prosthesis at the desired location within the body passageway by expanding a portion of the catheter associated with the prosthesis to force the prosthesis radially outwardly into contact with the body passageway, by deforming a portion of the prosthesis with a force in excess of the elastic limit of the portion of the prosthesis, to implant the prosthesis within the body passageway.

7. A method for expanding the lumen of a body passageway comprising the steps of:
   diposing an intraluminal graft upon a catheter;
   inserting the intraluminal graft and catheter within the body passageway by catheterization of the body passageway;
   delivering the intraluminal graft and catheter through the body passageway to a desired location within the body passageway without surgically exposing the desired location of the body passageway, *wherein the desired location in the body passageway is the location of an existing natural obstruction*; and
   expanding a portion of the catheter to provide controllable expansion of the intraluminal graft radially, outwardly into contact with the body passageway, by deforming a portion of the intraluminal graft with a force in excess of the elastic limit of the portion of the intraluminal graft, until the lumen of the body passageway at the desired location in the body passageway has been expanded, whereby the intraluminal graft prevents the body passageway from collapsing and decreasing the size of the expanded lumen, and the intraluminal graft remains in the body passageway.

*33. A method for implanting a balloon expandable stent prosthesis within a passageway of a coronary artery having an area of stenosis, comprising the steps of:*
   *disposing the stent prosthesis upon a catheter having an inflatable balloon portion,*
   *inserting the stent prosthesis and catheter within the body passageway by percutaneous catherization,*
   *delivering the catheter and stent prosthesis through the body passageway to the area of stenosis without surgically exposing the area of the body passageway; and*
   *providing controllable expansion of the stent prosthesis at the area of stenosis within the coronary artery passageway by expanding a portion of the inflatable balloon portion of the catheter associated with the stent prosthesis to force the stent prosthesis radially outwardly into contact with the area of stenosis in the body passageway, by deforming a portion of the stent prosthesis with a force in excess of the elastic limit of the portion of the stent prosthesis to implant the stent prosthesis within the body passageway at the area of stenosis.*

*34. In combination, a balloon expandable stent prosthesis for implantation in the passageway of a coronary artery having an area of stenosis and a catheter, comprising:*
   *an expandable stent prosthesis being a tubular shaped member having first and second ends and a smooth outer wall surface without any narrow, outwardly projecting edges, disposed between the first and second ends, the wall surface being formed by a plurality of intersecting elongate members, at least some of the elongate members intersecting with one another intermediate the first and second ends of the tubular shaped member;*
   *a catheter having an expandable, inflatable balloon portion;*
   *the tubular member being disposed on the balloon portion of the catheter;*
   *the tubular shaped member having a first diameter which permits intraluminal delivery of the tubular shaped member and the catheter into a lumen of a coronary artery having an area of stenosis;*
   *the tubular shaped member having a second, expanded diameter and a substantially smooth outer wall surface without any narrow outwardly projecting edges, upon the application from the interior of the tubular shaped member of a radially, outwardly extending force, which second diameter is variable and controlled by the amount of force applied to the tubular shaped member, at least some of the elongate members being deformed by the radially, outwardly extending force, to retain the tubular shaped member with the second, expanded diameter, whereby the tubular shaped member may be expanded to expand the coronary artery in the area of stenosis.*

\* \* \* \* \*